(12) United States Patent
Nelson et al.

(10) Patent No.: US 9,371,556 B2
(45) Date of Patent: Jun. 21, 2016

(54) SOLUTIONS, METHODS AND KITS FOR DEACTIVATING NUCLEIC ACIDS

(75) Inventors: Norman C. Nelson, San Diego, CA (US); Kenneth A. Browne, Poway, CA (US); Lizhong Dai, San Diego, CA (US); James Russell, Vista, CA (US); Mark E. Filipowsky, San Marcos, CA (US); Margarita B. Kaminsky, San Diego, CA (US); Daniel L. Kacian, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 1424 days.

(21) Appl. No.: 11/073,085

(22) Filed: Mar. 4, 2005

(65) Prior Publication Data

US 2005/0202491 A1    Sep. 15, 2005

Related U.S. Application Data

(60) Provisional application No. 60/550,749, filed on Mar. 5, 2004.

(51) Int. Cl.
*C12Q 1/68* (2006.01)
*A61L 2/18* (2006.01)
*C11D 3/395* (2006.01)

(52) U.S. Cl.
CPC .............. *C12Q 1/6802* (2013.01); *A61L 2/186* (2013.01); *C11D 3/3956* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 2,071,091 A | 2/1937 | Taylor | |
| 2,988,514 A | 6/1961 | Robson et al. | |
| 3,585,147 A | 6/1971 | Gordon | |
| 3,880,584 A | 4/1975 | Redmore | |
| 3,933,982 A | 1/1976 | Kushibe | |
| 3,943,261 A | 3/1976 | Amon et al. | |
| 3,951,840 A | 4/1976 | Fujino et al. | |
| 3,968,046 A | 7/1976 | Smeets | |
| 3,968,047 A | 7/1976 | Smeets | |
| 4,051,034 A | 9/1977 | Amon et al. | |
| 4,054,998 A | 10/1977 | Hesselgren | |
| 4,065,387 A | 12/1977 | Tsuneki et al. | |
| 4,084,747 A | 4/1978 | Alliger | |
| 4,113,645 A * | 9/1978 | DeSimone | 252/186.44 |
| 4,117,560 A | 10/1978 | Kidon et al. | |
| 4,122,192 A | 10/1978 | Fellows | |
| 4,123,376 A | 10/1978 | Gray | |
| 4,146,496 A | 3/1979 | Gray | |
| 4,150,024 A | 4/1979 | Syldatk et al. | |
| 4,151,052 A | 4/1979 | Goto et al. | |
| 4,172,773 A | 10/1979 | Pellegri et al. | |
| 4,175,011 A | 11/1979 | Spiliotis | |
| 4,216,027 A | 8/1980 | Wages | |
| 4,220,562 A | 9/1980 | Spadini et al. | |
| 4,235,332 A | 11/1980 | Andersen et al. | |
| 4,242,199 A | 12/1980 | Kelley | |
| 4,249,936 A | 2/1981 | Searle et al. | |
| 4,259,383 A | 3/1981 | Eggensperger et al. | |
| 4,276,263 A | 6/1981 | Andersen et al. | |
| 4,284,599 A | 8/1981 | Andersen et al. | |
| 4,288,367 A | 9/1981 | Day et al. | |
| 4,297,224 A | 10/1981 | Macchiarolo et al. | |
| 4,300,897 A | 11/1981 | Gray | |
| 4,311,598 A | 1/1982 | Verachtert | |
| 4,320,102 A | 3/1982 | Dalton, Jr. et al. | |
| 4,330,531 A | 5/1982 | Alliger | |
| 4,347,381 A | 8/1982 | Tuvell | |
| 4,357,254 A | 11/1982 | Kapiloff et al. | |
| 4,361,471 A | 11/1982 | Kosarek | |
| 4,370,241 A | 1/1983 | Junkermann et al. | |
| 4,370,490 A | 1/1983 | Gruber et al. | |
| 4,404,179 A | 9/1983 | Eastwood et al. | |
| 4,411,799 A | 10/1983 | Ito et al. | |
| 4,418,055 A | 11/1983 | Andersen et al. | |
| 4,432,856 A | 2/1984 | Murakami et al. | |
| 4,435,857 A | 3/1984 | Meloy | |
| 4,456,510 A | 6/1984 | Murakami et al. | |
| 4,459,150 A | 7/1984 | Hatton et al. | |
| 4,496,390 A | 1/1985 | Hatton et al. | |
| 4,496,470 A | 1/1985 | Kapiloff et al. | |
| 4,499,077 A | 2/1985 | Stockel et al. | |
| 4,505,904 A | 3/1985 | Sanborn | |
| 4,511,390 A | 4/1985 | Kauer | |
| 4,519,889 A | 5/1985 | Pellegri et al. | |
| 4,536,497 A | 8/1985 | Sanborn | |
| 4,539,179 A | 9/1985 | Meloy | |
| 4,545,784 A | 10/1985 | Sanderson | |
| 4,557,926 A | 12/1985 | Nelson et al. | |
| 4,559,158 A | 12/1985 | Hase et al. | |
| 4,569,769 A | 2/1986 | Walton et al. | |

(Continued)

FOREIGN PATENT DOCUMENTS

WO       02/060539 A    8/2002

OTHER PUBLICATIONS

Sigma Aldrich online 2007 catalog see attached pages info about chemical formula etc.*
PCT International Search Report, Application No. PCT/US2005/007153, Oct. 5, 2005.
US Peroxide, "Fenton's Reagent," http://www.h2o2.com/applications/industrialwastewater/fentonsreagent.html, accessed Dec. 10, 1997, 6 pages.
Blakely et al., "Hydrogen peroxide-Induced Base Damage in Deoxyribonucleic Acid", Radiation Research, 1990, 121:338-343, Academic Press, Inc., USA.
Bunton, "Nucleophilic Reactions of Peroxides," Peroxide Reaction Mechanisms, 1962, pp. 11-28, Interscience Publishers, New York, USA.

(Continued)

*Primary Examiner* — Suchira Pande
(74) *Attorney, Agent, or Firm* — Charles B. Cappellari; David L. Devemoe

(57) ABSTRACT

The present invention relates to reagents for use in deactivating nucleic acids and methods of making and using the same.

1 Claim, 23 Drawing Sheets

(56) References Cited

U.S. PATENT DOCUMENTS

| | | | |
|---|---|---|---|
| 4,592,892 A | 6/1986 | Ueno et al. | |
| 4,595,520 A | 6/1986 | Heile et al. | |
| 4,602,011 A | 7/1986 | West et al. | |
| 4,614,646 A | 9/1986 | Christiansen | |
| 4,654,208 A * | 3/1987 | Stockel et al. | 424/78.08 |
| 4,659,484 A | 4/1987 | Worley et al. | |
| 4,680,134 A | 7/1987 | Heile et al. | |
| 4,681,948 A | 7/1987 | Worley | |
| 4,690,772 A | 9/1987 | Tell et al. | |
| 4,731,222 A | 3/1988 | Kralovic et al. | |
| 4,766,113 A | 8/1988 | West et al. | |
| 4,767,542 A | 8/1988 | Worley | |
| 4,770,808 A | 9/1988 | McDonogh et al. | |
| 4,789,495 A | 12/1988 | Cahall et al. | |
| 4,822,513 A | 4/1989 | Corby | |
| 4,880,547 A | 11/1989 | Etani | |
| 4,911,856 A * | 3/1990 | Lokkesmoe et al. | 510/221 |
| 4,918,903 A | 4/1990 | Holston et al. | |
| 4,929,424 A | 5/1990 | Meier et al. | |
| 4,935,153 A | 6/1990 | Favstritsky et al. | |
| 4,966,690 A | 10/1990 | Gardiner et al. | |
| 4,966,716 A | 10/1990 | Favstritsky et al. | |
| 4,966,775 A | 10/1990 | Donofrio et al. | |
| 4,986,990 A | 1/1991 | Davidson et al. | |
| 4,995,987 A | 2/1991 | Whitekettle et al. | |
| 5,034,150 A | 7/1991 | Smith | |
| 5,039,383 A | 8/1991 | Spotnitz et al. | |
| 5,045,222 A | 9/1991 | Endo et al. | |
| 5,047,164 A | 9/1991 | Corby | |
| 5,057,612 A | 10/1991 | Worley et al. | |
| 5,077,008 A | 12/1991 | Kralovic et al. | |
| 5,098,447 A | 3/1992 | Zucchini et al. | |
| 5,106,616 A | 4/1992 | McAnalley et al. | |
| 5,112,521 A | 5/1992 | Mullins et al. | |
| 5,124,359 A | 6/1992 | Wachman et al. | |
| 5,126,057 A | 6/1992 | Worley et al. | |
| 5,129,999 A | 7/1992 | Holland et al. | |
| 5,167,866 A | 12/1992 | Hwa et al. | |
| 5,202,047 A | 4/1993 | Corby | |
| 5,204,368 A | 4/1993 | Cronje et al. | |
| 5,208,057 A | 5/1993 | Greenley et al. | |
| 5,211,927 A | 5/1993 | Itani et al. | |
| 5,217,686 A | 6/1993 | Vanderpool et al. | |
| 5,236,600 A | 8/1993 | Hutchins | |
| 5,236,626 A | 8/1993 | Vanderpool et al. | |
| 5,238,843 A | 8/1993 | Carpenter et al. | |
| 5,256,268 A | 10/1993 | Goto et al. | |
| 5,258,304 A | 11/1993 | Carpenter et al. | |
| 5,266,587 A | 11/1993 | Sankey et al. | |
| 5,279,758 A | 1/1994 | Choy | |
| 5,294,541 A | 3/1994 | Kaplan et al. | |
| 5,296,518 A | 3/1994 | Grasel et al. | |
| 5,312,586 A | 5/1994 | Stockel | |
| 5,324,477 A | 6/1994 | Schroeder et al. | |
| 5,338,461 A | 8/1994 | Jones | |
| 5,338,748 A | 8/1994 | Wachman et al. | |
| 5,344,838 A | 9/1994 | Wachman et al. | |
| 5,350,563 A | 9/1994 | Kralovic et al. | |
| 5,356,803 A | 10/1994 | Carpenter et al. | |
| 5,366,004 A | 11/1994 | Garner et al. | |
| 5,366,694 A | 11/1994 | Stockel | |
| 5,374,368 A | 12/1994 | Hauschild | |
| 5,385,650 A | 1/1995 | Howarth et al. | |
| 5,395,541 A | 3/1995 | Carpenter et al. | |
| 5,407,656 A | 4/1995 | Roozdar | |
| 5,407,685 A | 4/1995 | Malchesky et al. | |
| 5,407,949 A | 4/1995 | Wachman et al. | |
| 5,411,585 A | 5/1995 | Avery et al. | |
| 5,419,836 A | 5/1995 | Ray et al. | |
| 5,424,032 A | 6/1995 | Christensen et al. | |
| 5,424,060 A | 6/1995 | Hauschild | |
| 5,424,079 A | 6/1995 | Yu | |
| 5,424,323 A | 6/1995 | Wachman et al. | |
| 5,462,692 A | 10/1995 | Roesler et al. | |
| 5,464,636 A | 11/1995 | Hight et al. | |
| 5,476,670 A | 12/1995 | Hight et al. | |
| 5,489,390 A | 2/1996 | Sivik et al. | |
| 5,498,415 A | 3/1996 | Jones | |
| 5,506,335 A | 4/1996 | Uhr et al. | |
| 5,512,206 A | 4/1996 | Steltenkamp et al. | |
| 5,523,023 A | 6/1996 | Kleinstück et al. | |
| 5,527,547 A | 6/1996 | Hight et al. | |
| 5,547,584 A | 8/1996 | Capehart | |
| 5,576,028 A | 11/1996 | Martin et al. | |
| 5,578,134 A | 11/1996 | Lentsch et al. | |
| 5,591,692 A | 1/1997 | Jones et al. | |
| 5,603,911 A | 2/1997 | Korvela et al. | |
| 5,607,619 A | 3/1997 | Dadgar et al. | |
| 5,607,698 A | 3/1997 | Martin et al. | |
| 5,612,200 A | 3/1997 | Dattagupta et al. | |
| 5,614,528 A | 3/1997 | Jones et al. | |
| 5,616,234 A | 4/1997 | Rhees et al. | |
| 5,620,585 A | 4/1997 | Dadgar et al. | |
| 5,624,575 A | 4/1997 | Meade et al. | |
| 5,630,883 A | 5/1997 | Steer et al. | |
| 5,631,300 A | 5/1997 | Wellinghoff | |
| 5,635,195 A | 6/1997 | Hall, II et al. | |
| 5,639,295 A | 6/1997 | Wellinghoff et al. | |
| 5,654,269 A | 8/1997 | Dankowski et al. | |
| 5,662,866 A | 9/1997 | Siegel et al. | |
| 5,662,940 A | 9/1997 | Hight et al. | |
| 5,668,185 A | 9/1997 | Wellinghoff | |
| 5,670,451 A | 9/1997 | Jones et al. | |
| 5,672,266 A | 9/1997 | Sivik et al. | |
| 5,676,933 A | 10/1997 | Hauschild | |
| 5,688,385 A | 11/1997 | Rhees et al. | |
| 5,688,515 A | 11/1997 | Kuechler et al. | |
| 5,688,756 A | 11/1997 | Garabedian, Jr. et al. | |
| 5,705,467 A | 1/1998 | Choy | |
| 5,716,569 A | 2/1998 | Berenbold et al. | |
| 5,723,095 A | 3/1998 | Fricker et al. | |
| 5,725,887 A | 3/1998 | Martin et al. | |
| 5,726,280 A | 3/1998 | Uhr et al. | |
| 5,731,282 A | 3/1998 | Duquesne | |
| 5,741,952 A | 4/1998 | Sanderson et al. | |
| 5,756,440 A | 5/1998 | Watanabe et al. | |
| 5,780,064 A | 7/1998 | Meisters et al. | |
| 5,783,146 A | 7/1998 | Williams, Jr. | |
| 5,785,887 A | 7/1998 | Steltenkamp et al. | |
| 5,801,138 A | 9/1998 | Croud et al. | |
| 5,807,585 A | 9/1998 | Martin et al. | |
| 5,824,531 A | 10/1998 | Outtrup et al. | |
| 5,839,258 A | 11/1998 | Takayanagi et al. | |
| 5,840,343 A | 11/1998 | Hall, II et al. | |
| 5,851,421 A | 12/1998 | Choy et al. | |
| 5,856,164 A | 1/1999 | Outtrup et al. | |
| 5,856,167 A | 1/1999 | Outtrup | |
| 5,858,443 A | 1/1999 | Hei et al. | |
| 5,882,526 A | 3/1999 | Brown et al. | |
| 5,900,256 A | 5/1999 | Scoville, Jr. et al. | |
| 5,910,420 A | 6/1999 | Tuompo et al. | |
| 5,922,745 A | 7/1999 | McCarthy et al. | |
| 5,931,172 A | 8/1999 | Steer et al. | |
| 5,942,152 A | 8/1999 | Tafesh et al. | |
| 5,948,742 A | 9/1999 | Chang et al. | |
| 5,958,853 A | 9/1999 | Watanabe | |
| 5,972,238 A | 10/1999 | Rimpler et al. | |
| 5,976,386 A | 11/1999 | Barak | |
| 5,981,461 A | 11/1999 | Counts et al. | |
| 5,997,764 A | 12/1999 | Ambuter et al. | |
| 5,997,814 A | 12/1999 | Minerovic et al. | |
| 6,037,318 A | 3/2000 | Na et al. | |
| 6,054,054 A | 4/2000 | Robertson et al. | |
| 6,063,884 A | 5/2000 | Egraz et al. | |
| 6,080,710 A | 6/2000 | Withenshaw et al. | |
| 6,083,422 A | 7/2000 | Ambuter et al. | |
| 6,086,785 A | 7/2000 | Roesler et al. | |
| 6,090,770 A | 7/2000 | Mendoza et al. | |
| 6,099,861 A | 8/2000 | DeSenna et al. | |
| 6,103,950 A | 8/2000 | Rimpler et al. | |
| 6,117,285 A | 9/2000 | Welch et al. | |
| 6,123,933 A | 9/2000 | Hayama et al. | |
| 6,126,755 A | 10/2000 | Colgan et al. | |
| 6,132,521 A | 10/2000 | Gupta et al. | |

(56) References Cited

U.S. PATENT DOCUMENTS

| | | | |
|---|---|---|---|
| 6,132,628 A | 10/2000 | Barak | |
| 6,132,825 A | 10/2000 | Frisk | |
| 6,133,216 A | 10/2000 | Löffler et al. | |
| 6,140,294 A | 10/2000 | Delroisse et al. | |
| 6,149,835 A | 11/2000 | Brown | |
| 6,150,318 A | 11/2000 | Silvester et al. | |
| 6,165,318 A | 12/2000 | Paren et al. | |
| 6,165,963 A | 12/2000 | Delroisse et al. | |
| 6,171,551 B1 | 1/2001 | Malchesky et al. | |
| 6,176,937 B1 | 1/2001 | Colgan et al. | |
| 6,184,321 B1 | 2/2001 | Egraz et al. | |
| 6,197,814 B1 | 3/2001 | Arata | |
| 6,203,767 B1 | 3/2001 | Leasko | |
| 6,207,108 B1 | 3/2001 | Carr et al. | |
| 6,207,201 B1 | 3/2001 | Piacenza | |
| 6,210,639 B1 | 4/2001 | Vlass et al. | |
| 6,218,351 B1 | 4/2001 | Busch et al. | |
| 6,255,266 B1 | 7/2001 | Gupta et al. | |
| 6,257,253 B1 | 7/2001 | Lentsch et al. | |
| 6,259,758 B1 | 7/2001 | Kim et al. | |
| 6,262,013 B1 | 7/2001 | Smith et al. | |
| 6,267,885 B1 | 7/2001 | Briggs et al. | |
| 6,270,690 B1 | 8/2001 | Himmrich et al. | |
| 6,274,542 B1 | 8/2001 | Carr et al. | |
| 6,302,968 B1 | 10/2001 | Baum et al. | |
| 6,306,812 B1 | 10/2001 | Perkins et al. | |
| 6,322,748 B1 | 11/2001 | Hutton et al. | |
| 6,322,749 B1 | 11/2001 | McCarthy et al. | |
| 6,325,968 B1 | 12/2001 | Fricker et al. | |
| 6,346,279 B1 | 2/2002 | Rochon | |
| 6,361,787 B1 | 3/2002 | Shaheen et al. | |
| 6,387,858 B1 | 5/2002 | Shah et al. | |
| 6,387,862 B2 | 5/2002 | Busch et al. | |
| 6,399,557 B2 | 6/2002 | Perkins et al. | |
| 6,410,497 B1 | 6/2002 | Kappes et al. | |
| 6,415,010 B2 | 7/2002 | Kim et al. | |
| 6,419,879 B1 | 7/2002 | Cooper et al. | |
| 6,423,868 B1 | 7/2002 | Carr et al. | |
| 6,426,317 B1 | 7/2002 | Garris et al. | |
| 6,447,722 B1 | 9/2002 | Rakestraw | |
| 6,448,062 B1 | 9/2002 | Huth et al. | |
| 6,464,868 B1 | 10/2002 | Korin | |
| 6,468,469 B2 | 10/2002 | Huth | |
| 6,478,972 B1 | 11/2002 | Shim et al. | |
| 6,478,973 B1 | 11/2002 | Barak | |
| 6,508,929 B1 | 1/2003 | Mercer | |
| 6,517,730 B1 | 2/2003 | Rex | |
| 6,565,893 B1 | 5/2003 | Jones et al. | |
| 6,974,790 B2 * | 12/2005 | Zabarylo et al. | 510/446 |
| 2004/0101881 A1 * | 5/2004 | Durmowicz et al. | 435/6 |

OTHER PUBLICATIONS

Edwards, "Nucleophilic Displacement on Oxygen in Peroxides," Peroxide Reaction Mechanisms, 1962, pp. 67-105 Interscience Publishers, New York, USA.

Feig et al., "Reverse chemical mutagenesis: Identification of the mutagenic lesions resulting from reactive oxygen species-mediated damage to DNA," Proc. Natl. Acad. Sci. USA, 1994, 91:6609-6613, National Academy of Sciences, USA.

Galwey et al., "Thermal Decomposition of Sodium Carbonate Perhydrate in the Presence of Liquid Water," J. Chem. Soc., Faraday Trans. 1, 1982, 78:2815-2827, American Chemical Society, USA.

Khan, "Quantitative Generation of Singlet ($^1\Delta_g$) Oxygen from Acidified Aqueous Peroxynitrite Produced by the Reaction of Nitric Oxide and Superoxide Anion," J. Biolumin. Chemilumin., 1995, 10:329-333, Wiley & Sons, UK.

Luo et al., "Three chemically distinct types of oxidants formed by iron-mediated Fenton reactions in the presence of DNA," Proc. Natl. Acad. Sci. USA, 1994, 91:12438-12442, National Academy of Sciences, USA.

McKillop et al., "Sodium Perborate and Sodium Percarbonate: Cheap, Safe and Versatile Oxidising Agents for Organic Synthesis," Tetrahedron, 1995, 51(22):6145-6166, Elsevier Science Ltd., UK.

Muzart, "Sodium Perborate and Sodium Percarbonate in Organic Synthesis," Synthesis, 1995, pp. 1325-1347; Academic Press, USA.

Neta et al., "Rate Constants for Reactions of Peroxyl Radicals in Fluid Solutions,", J. Phys. Chem. Ref. Data, 1990, 19(2):413-513, American Chemical Society, USA.

Russell, "Peroxide Pathways in Autoxidation," Peroxide Reaction Mechanisms, 1962, pp. 107-128, Interscience Publishers, New York, USA.

Shanley, "Hydrogen Peroxide," Peroxide Reaction Mechanisms, 1962, pp. 129-136, Interscience Publishers, New York, USA.

Snarskaya, "Fenton Reaction," http://alpha.genebee.msu.su/agenzymes/antox/oxr-react/fenton/fenton.html, accessed Dec. 10, 1997, 6 pages.

Vol'Nov, "Classification and Nomenclature of Inorganic Peroxide Compounds," Peroxides, Superoxides, and Ozonides of Alkali and Alkaline Earth Metals, 1966, Ch. 1, pp. 9-20, Plenum Press, New York, USA.

Vol'Nov, "Peroxides of the Group One Metals of the Periodic Table," Peroxides, Superoxides, and Ozonides of Alkali and Alkaline Earth Metals, 1966, Ch. 2, pp. 21-55, Plenum Press, New York, USA.

Vol'Nov, "Peroxides of the Group Two Elements of the Periodic Table," Peroxides, Superoxides, and Ozonides of Alkali and Alkaline Earth Metals, 1966, Ch. 3, pp. 57-89, Plenum Press, New York, USA.

Whiteman et al., "Hypochlorous Acid-Induced Base Modifications in Isolated Calf Thymus DNA," Chem. Res. Toxicol., 1997, 10:1240-1246, American Chemical Society, USA.

Wink et al., "The Fenton oxidation mechanism: Reactivities of biologically relevant substrates with two oxidizing intermediates differ from those predicted for the hydroxyl radical," Proc. Natl. Acad. Sci. USA, 1994, 91:6604-6608, National Academy of Sciences, USA.

APO Office Action, Australian Patent Application No. 2005222069, Aug. 13, 2009.

Extended European Search Report, Application No. EP 100 11173.1, Jan. 21, 2011.

JPO Office Action and Translation, Japanese Patent Application No. 2007-502029, Aug. 9, 2011.

* cited by examiner

Figure 9C Control
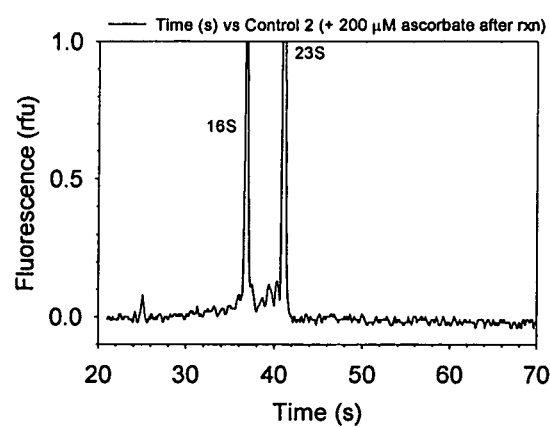
Figure 9D 15 μM HOCl
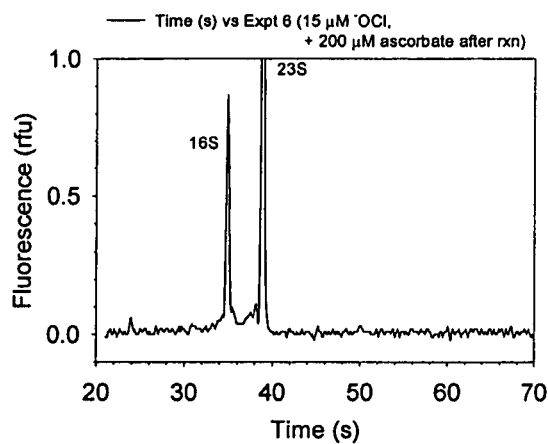
Figure 9E 150 μM HOCl
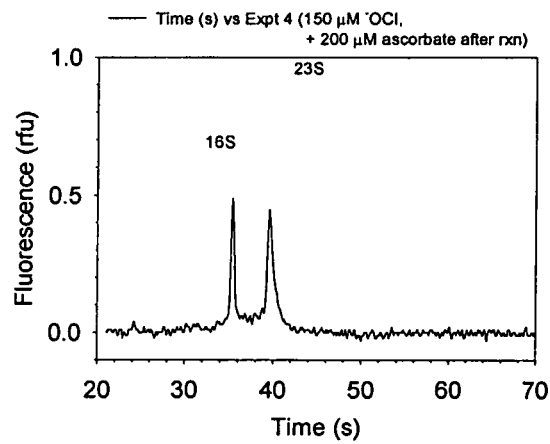
Figure 9F 1.5 mM HOCl
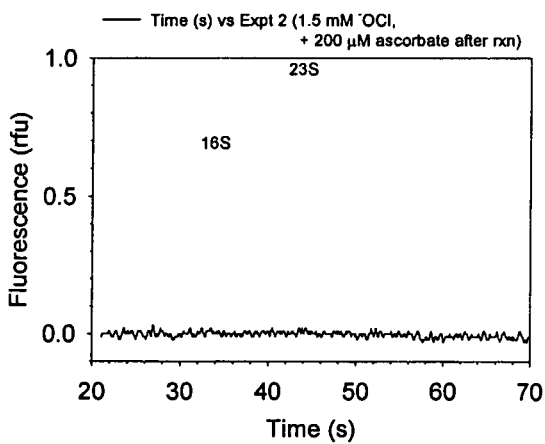

Figure 9G 16S rRNA
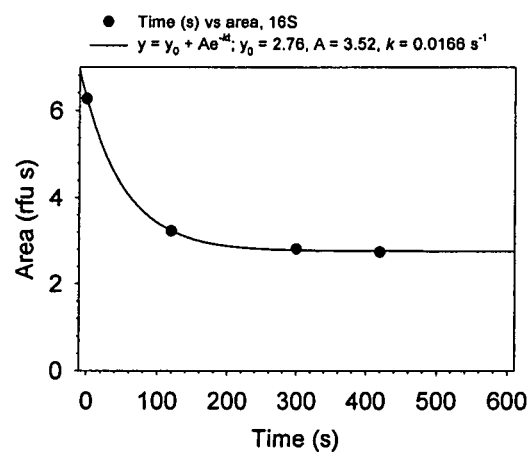
Figure 9H 23S rRNA
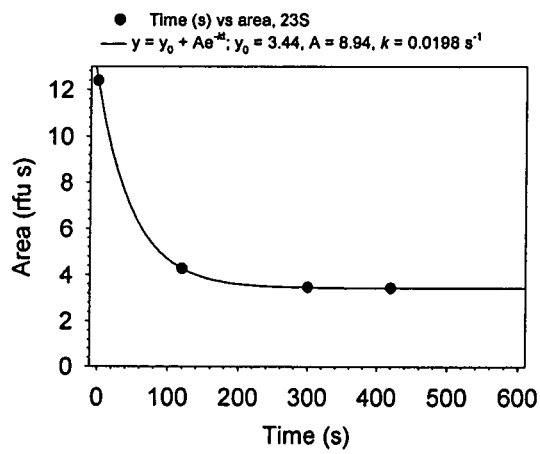

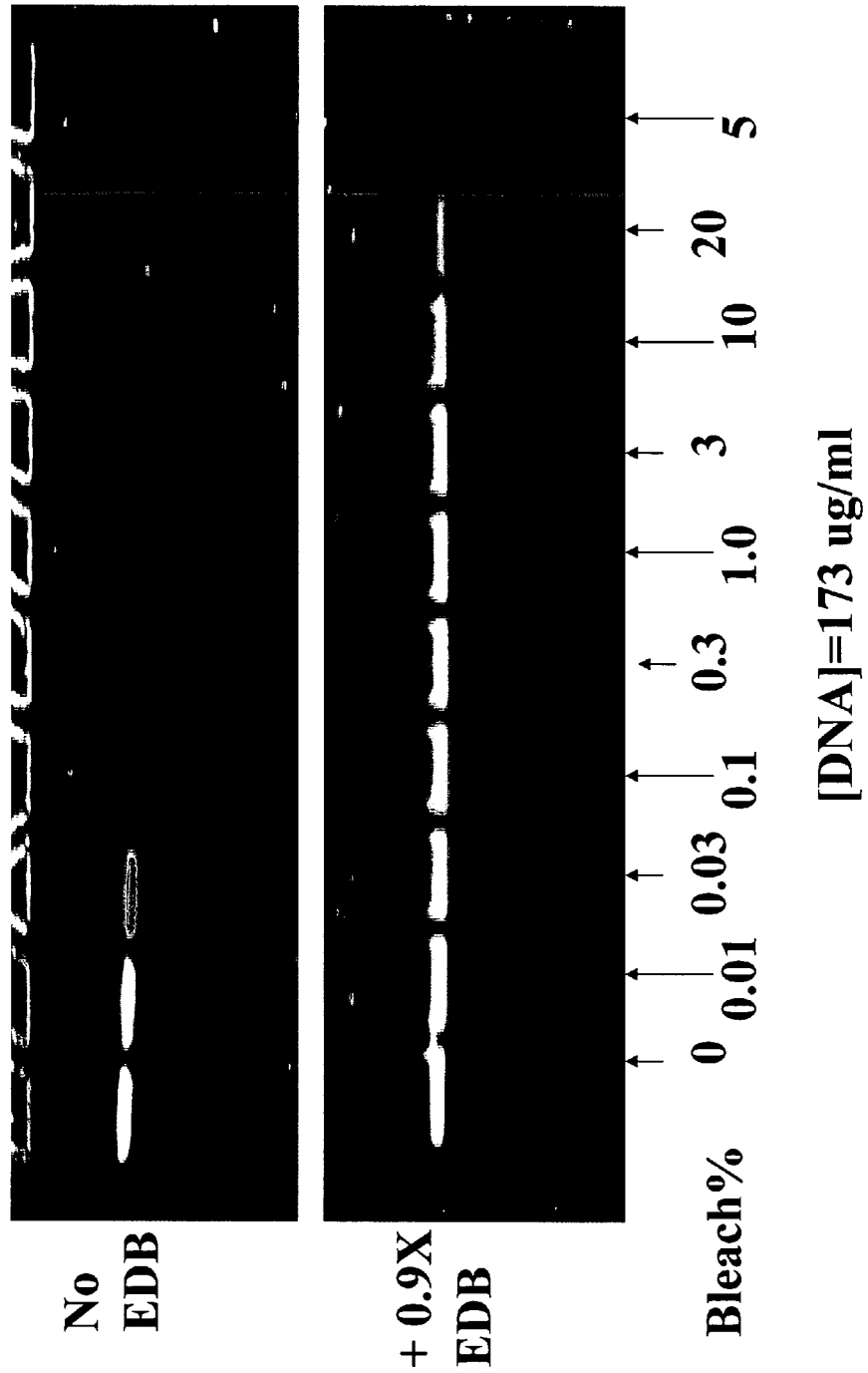
Figure 11A Scavenging effect of Enzyme Dilution Buffer

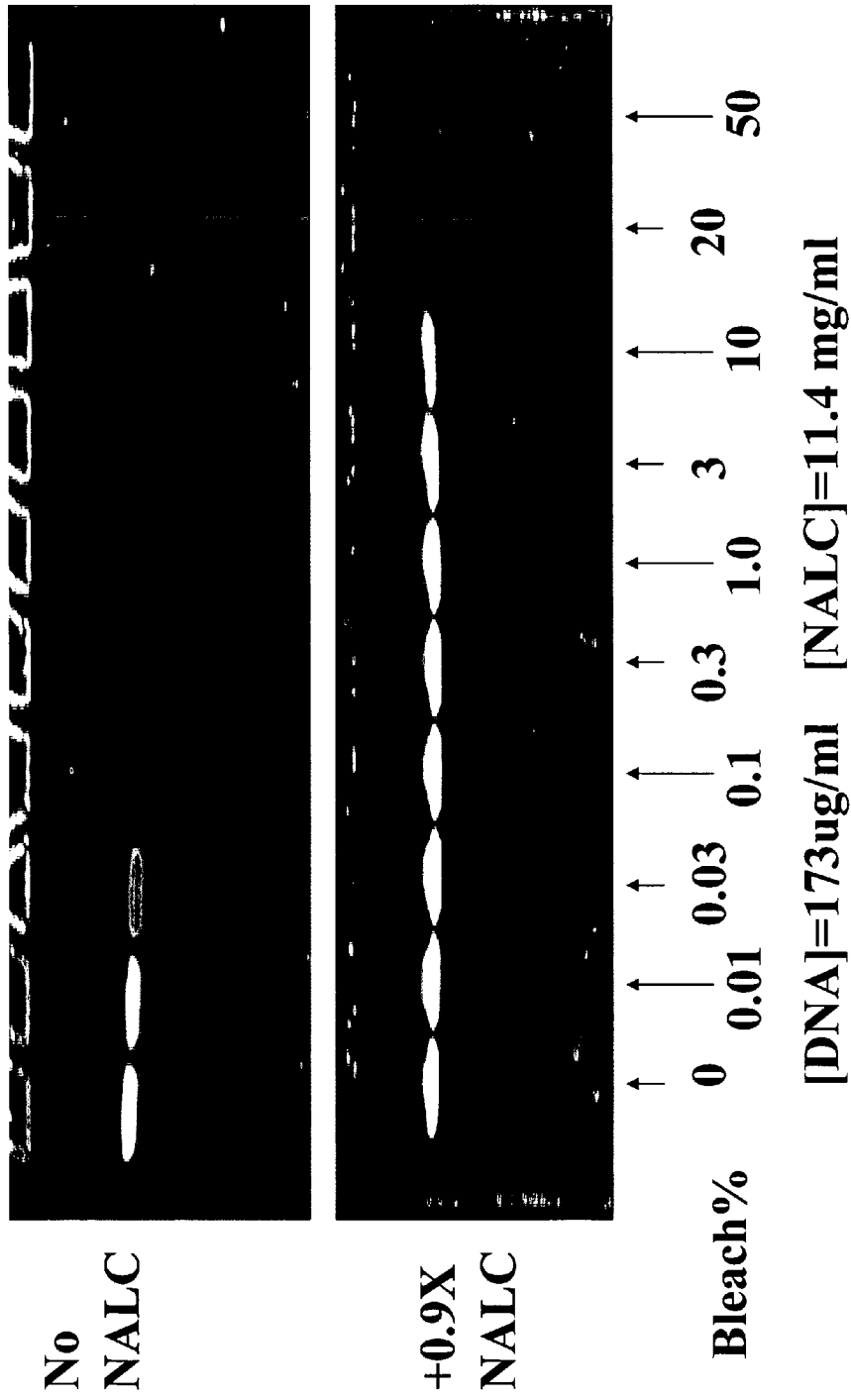

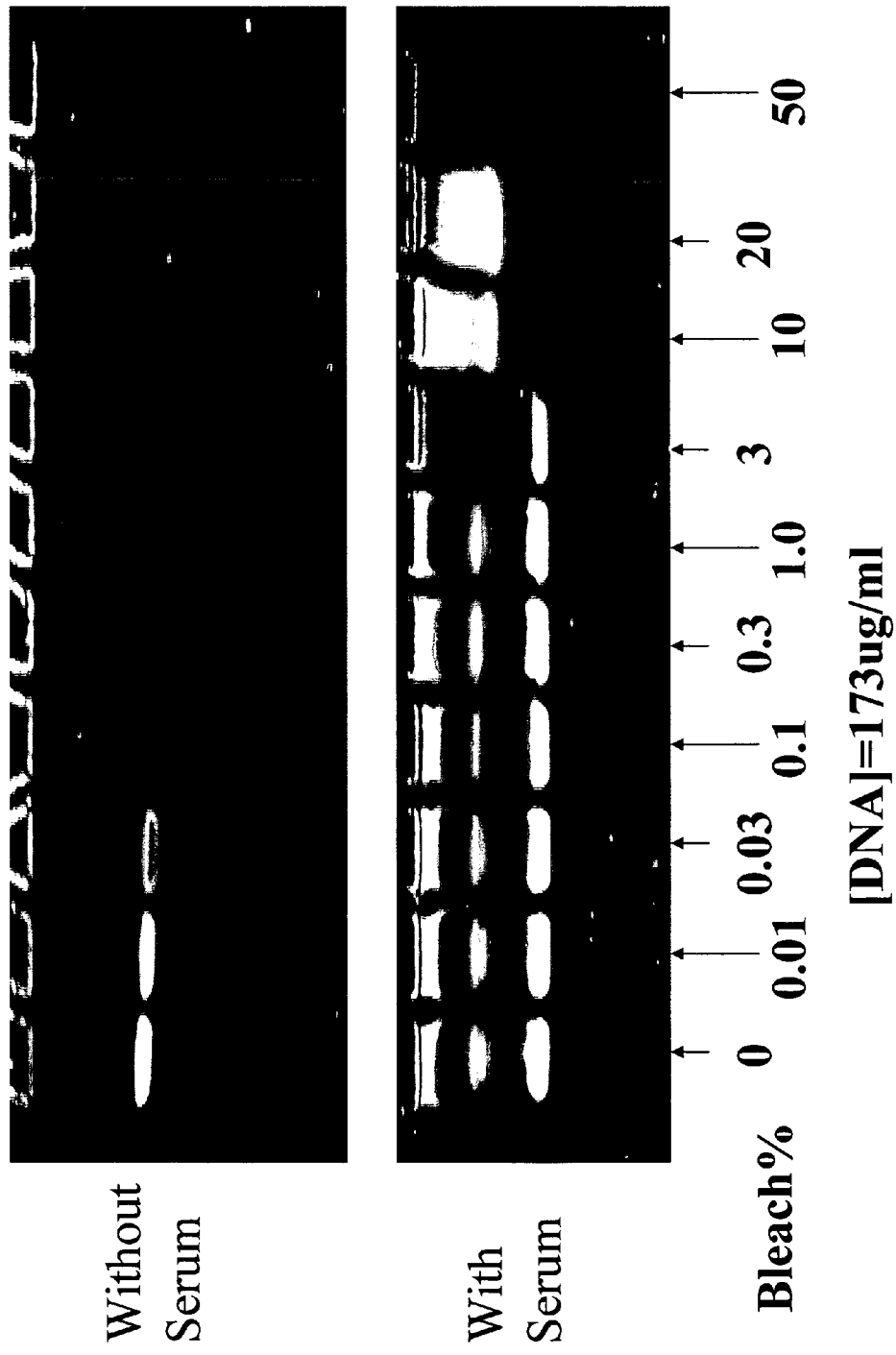
Figure 11C Scavenging effect of Serum: Fixed amount of DNA with or w/o Serum plus different concentration of bleach solutions

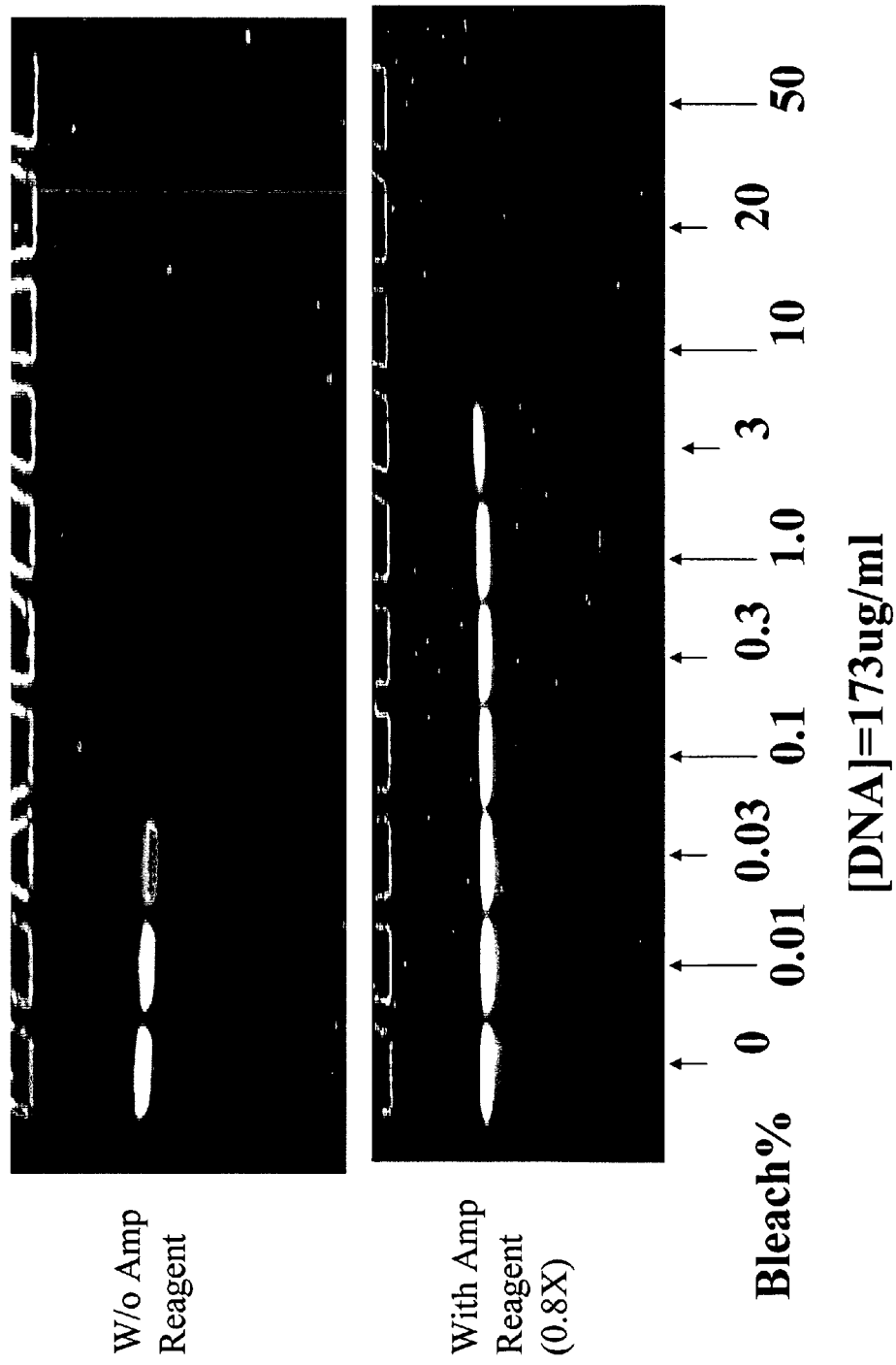
Figure 11D Scavenging effect of Amp Reagent: Fixed amount of DNA with or w/o Amp Reagent plus different concentration of bleach solutions

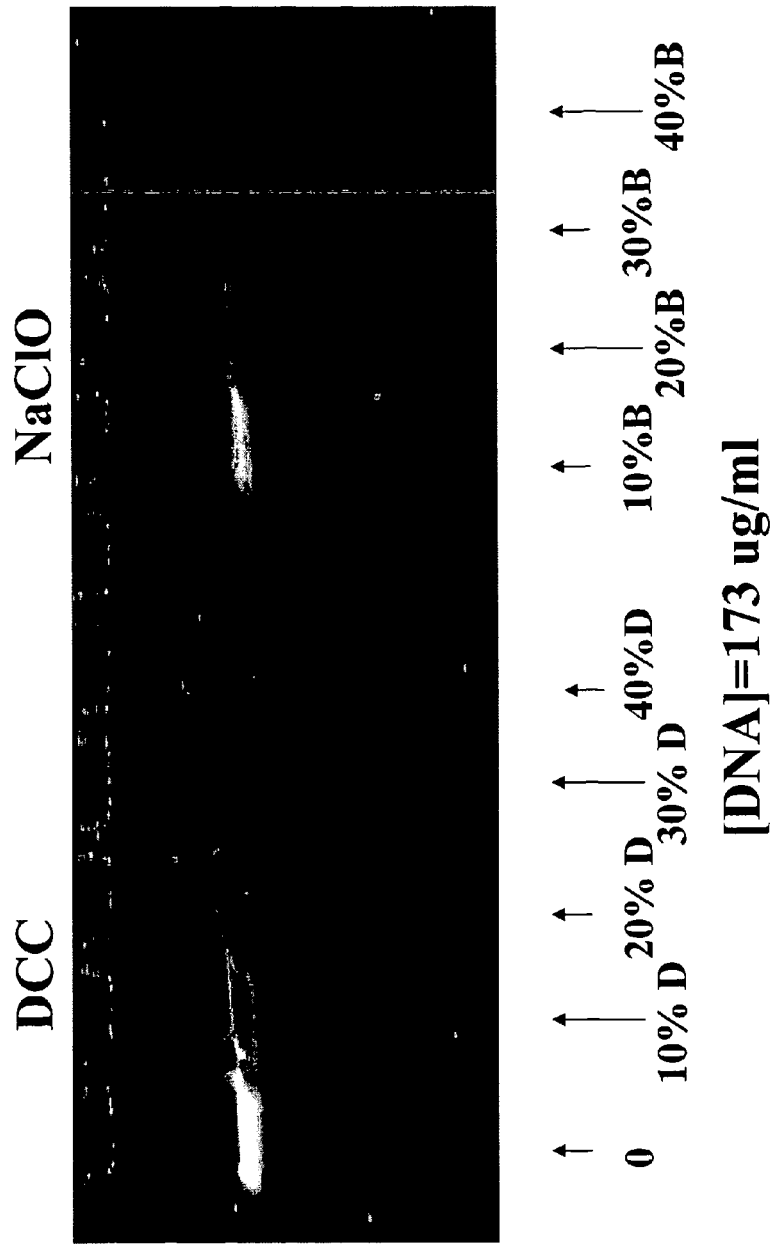
Figure 12: Scavenging effect of EDB
Fixed amount of DNA in 0.8XEDB plus different concentration of bleach or DCC solution

SOLUTIONS, METHODS AND KITS FOR DEACTIVATING NUCLEIC ACIDS

RELATED APPLICATION

This application claims the benefit of U.S. Provisional Patent Application No. 60/550,749, filed on Mar. 5, 2004, the contents of which are hereby incorporated herein by reference in their entirety.

FIELD OF THE INVENTION

The present invention relates to formulations, methods and kits containing or employing an agent for use in deactivating nucleic acids present on a surface or in a solution.

BACKGROUND

Procedures for qualitatively or quantitatively determining the presence of particular organisms or viruses in a test sample routinely rely upon nucleic acid-based probe testing. To increase the sensitivity of these procedures, an amplification step is often included to increase the copy number of potential nucleic acid target sequences present in the test sample. During amplification, polynucleotide chains containing the target sequence and/or its complement are synthesized in a template-dependent manner from ribonucleoside or deoxynucleoside triphosphates using nucleotidyltransferases known as polymerases. There are many amplification procedures in general use today, including the polymerase chain reaction (PCR), Q-beta replicase, self-sustained sequence replication (3SR), transcription-mediated amplification (TMA), nucleic acid sequence-based amplification (NASBA), ligase chain reaction (LCR), strand displacement amplification (SDA) and loop-mediated isothermal amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., Nucleic Acids Res., 20:1691-1696 (1992); Fahy et al., "Self-sustained Sequence Replication (3SR): An Isothermal Transcription-Based Amplification System Alternative to PCR," PCR Methods and Applications, 1:25-33 (1991); Kacian et al., "Nucleic Acid Sequence Amplification Methods," U.S. Pat. No. 5,399,491; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," U.S. Pat. No. 6,410,278; Dattagupta et al., "Isothermal Strand Displacement Amplification," U.S. Pat. No. 6,214,587; and Lee et al., *Nucleic Acid Amplification Technologies: Application To Disease Diagnosis* (1997).

Nucleic acid products formed during an amplification procedure (i.e., amplicon) can be analyzed either during the course of the amplification reaction (real-time) or once the amplification reaction has been generally completed (end-point) using detectable probes. While the probes are designed to screen for target-containing amplicon, other products may be produced during an amplification procedure (e.g., primer-dimers formed in a typical PCR reaction) that have the potential to interfere with the desired amplification reaction. Following completion of the amplification procedure and exposure to detectable probes, the resulting reaction mixture is discarded.

During the steps of an assay or synthesis procedure which includes an amplification procedure, it is possible to contaminate work surfaces or laboratory equipment with nucleic acids used or formed in the assay through spills, mishandling, aerosol formation, etc. This nucleic acid can then carry-over and contaminate future amplification and other nucleic acid assay procedures performed using the same laboratory equipment and/or on the same work surfaces. The presence of carryover products can result in the unwanted consumption of amplification reagents or, in the case of target-containing amplicon from a previous amplification procedure, it can lead to an erroneous result, as amplification procedures are capable of detecting the presence of even minute amounts of target nucleic acid. In the case of a synthetic amplification reaction, the desired nucleic acid product may become contaminated by carry-over products and/or synthesis yields may be reduced.

Various methods have been devised to limit carryover contamination. A PCR amplification product, for example, can be deactivated from further amplification by irradiation with UV light. See Ou et al., BioTechniques, 10:442-446 (1991); and Cimino et al., Nucleic Acids Res., 19:99-107 (1991). Such irradiation in the absence or presence of a DNA binding photoactivatable ligand (e.g., isopsoralen) makes the product DNA nonamplifiable but retains the specific hybridization property. In addition, use of a 3'-ribose primer in a PCR reaction produces nucleic acid that can be readily destroyed by an alkali (e.g., NaOH). See Walder et al., Nucleic Acids Res., 21:4339-4343 (1993). Similarly, other procedures are used to produce specific modified nucleic acids that can be selectively destroyed by treatment with a specific enzyme. Such modified nucleic acids have been produced by amplification in the presence of dUTP as a substrate in a PCR reaction. Deoxy U-containing product DNA can be deactivated by a U-specific enzyme making the DNA nonamplifiable. See Integrated DNA Technologies Technical Bulletin, Triple C primers (1992); and Longo et al., Gene, 93:125-128 (1990). Many of these methods function well with DNA but require expensive reagents and affect the course of the amplification procedure (e.g., requiring longer times and specific reagents).

In a preferred method, work surfaces and laboratory equipment exposed to nucleic acid products are treated with a 50% bleach solution (i.e., a bleach solution containing about 2.5% to about 3.25% (w/v) sodium hypochlorite) to deactivate nucleic acids. See GEN-PROBE® APTIMA COMBO 2® Assay Package Insert, IN0037 Rev. A/2003-08. While this bleach solution is effective at deactivating nucleic acids present on treated surfaces, it tends to create noxious fumes in poorly ventilated areas and corrodes laboratory equipment over time. Therefore, it is an object of the present invention to provide a formulation containing a nucleic acid deactivating agent that is stable in solution, has a tolerable odor, and which is non-corrosive or is substantially less corrosive than a standard 50% bleach solution.

SUMMARY

The present invention satisfies this objective by providing a formulation that contains or can be combined with a nucleic acid deactivating agent ("deactivating agent") in an amount sufficient to deactivate nucleic acids contacted with the formulation in solution or on a solid surface. By "deactivate" is meant that the nucleic acid is altered such that it can no longer function as it did prior to deactivation. For example, the nucleic acid may no longer be capable of acting as a template in, or otherwise interfering with (e.g., through the formation of primer-dimers), an amplification reaction, binding to another nucleic acid or protein, or serving as a substrate for an enzyme. The term "deactivate" does not imply any particular mechanism by which the deactivating agent of the formulation alters nucleic acids. The components of the formulation include a corrosion-inhibiting agent, a wetting agent, a solubilizing agent and, optionally, a deactivating agent. When the formulation is comprised of all four components, the corrosion-inhibiting agent is present in an amount sufficient to reduce the corrosiveness of the deactivating agent, the wetting agent is present in an amount sufficient to improve the dispersion properties of the deactivating agent and/or to increase the solubility of the deactivating agent and/or other material present on a solid surface or in a solution, the solubilizing agent is present in an amount sufficient to increase the solubility of the deactivating agent, or the corrosion inhibiting agent, or the wetting agent, or various combinations thereof, and the deactivating agent is present in an amount sufficient to substantially deactivate nucleic acids contacted with the formulation. If the formulation does not include the deactivating agent, then the amounts of the corrosion-inhibiting agent, the wetting agent and the solubilizing agent are concentrated to account for their decreased concentrations when combined with the deactivating agent and any diluents (e.g., water) which may be used to form a final working solution capable of deactivating nucleic acids.

Deactivating agents of the present invention are selected for their ability to substantially deactivate nucleic acids present on a surface or in a solution, thereby preventing the nucleic acids from acting as unintended templates in an amplification reaction or otherwise contaminating a workspace, laboratory equipment or materials, or working solutions. For certain applications, the deactivating agents of the present invention may be used without the corrosion-inhibiting agent, the wetting agent and/or the solubilizing agent referred to above. Preferred deactivating agents include bleach, sodium hypochlorite (NaOCl) (or hypochlorous acid (HOCl), which results when chlorine ions are combined with water), sodium hypochlorite and sodium bromide (NaBr), dichloroisocyanurate (DCC), hydrogen peroxide ($H_2O_2$) and metal ions, preferably copper ions ($Cu^{++}$) (e.g., cupric sulfate ($CuSO_4$) or cupric acetate ($Cu(CH_3COO)_2.H_2O$)), hydrogen peroxide in combination with metal ions and piperazine or piperazine-containing formulations, acetate or ascorbate, percarbonate ($2Na_2CO_3.3H_2O_2$), peroxymonosulfate ($KHSO_5$), peroxymonosulfate and potassium bromide (KBr), hypobromite ions (OBr-) (e.g., hypobromous acid (HOBr)) and halohydantoins (e.g., 1,3-dihalo-5,5-dimethylhydantoins). Hypochlorite and hypobromite ions may be delivered to a solution using a salt, such as sodium. Particularly preferred are deactivating agents containing chloronium ions ($Cl^+$), such as sodium hypochlorite, a component of household bleach, or DCC. The DCC may be substantially pure or it may be part of a DCC-containing solution, such as ACT 340 PLUS 2000® disinfectant, containing sodium dichloroisocyanurate dihydrate at 40% p/p. An advantage of DCC is that it is less corrosive and, in some cases, more resistant to inactivation by contaminating organic material than hypochlorite.

While the deactivating agents of the present invention may be provided, alone or as part of a formulation, in any amount sufficient to deactivate nucleic acids, preferred concentration ranges of above-described deactivating agents are as follows: (i) from about 0.06% to about 3% (w/v), about 0.18% to about 1.8% (w/v), about 0.6% to about 1.5% (w/v), or about 0.6% to about 1.2% (w/v) sodium hypochlorite, or sodium hyphochlorite and sodium bromide, where the sodium hypochlorite:sodium bromide ratio is about 5:1 to about 1:5, about 2:1 to about 1:2, or about 1:1; (ii) from about 5 mM to about 400 mM, about 10 mM to about 200 mM, about 20 mM to about 100 mM, or about 40 mM to about 80 mM DCC; (iii) from about 100 mM to about 880 mM, about 200 mM to about 880 mM, or about 250 mM to about 800 mM percarbonate; (iv) from about 50 mM to about 300 mM or about 100 mM to about 200 mM peroxymonosulfate or peroxymonosulfate and potassium bromide, where the peroxymonosulfate:potassium bromide ratio is about 2:1 to about 1:2 or about 1:1. These ranges reflect concentrations in final working solutions to be used directly on a surface or in a solution and may be adjusted where the formulation is a concentrate. The preferred concentration ranges of hydrogen peroxide containing formulations are described below.

When chlorine is a component of the deactivating agent (e.g., sodium hypochlorite or DCC), the potential organic load on a surface or in a solution that will be exposed to the deactivating agent is a factor in determining the concentration of the chlorine-containing component. This is because organic materials, especially compounds containing primary amine and sulfhydryl groups, react with chloronium ions and effectively scavenge them from solution. Therefore, when selecting the concentration of the chlorine containing component to use in the formulation for deactivating nucleic acids, consideration must be given not only to the expected amount of nucleic acid on the surface or in the solution to be treated, but also to the expected organic load, as well as sources of interfering substances of a non-organic origin. Interfering substances may also affect non-chlorine based deactivating agents and, for this reason, their influence on a deactivating agent should be evaluated when determining the concentration of the deactivating agent needed to deactivate nucleic acids on a surface or in a solution.

The wetting agent is included in the formulation to ensure that the deactivating agent makes sufficient contact with the surface being treated and/or to improve the solubility of the deactivating agent and/or other material that may be present on a surface or in a solution to be decontaminated (e.g., nucleic acids, organic substances, oils or films, etc.). Detergents and surfactants are preferred wetting agents because they reduce surface tension and allow for more complete wetting of surfaces with the deactivating agent. Additionally, detergents and surfactants help to solubilize materials to be removed from surfaces or deactivated in a solution. But because detergents and surfactants tend to foam, detergent and surfactant types and concentrations should be selected to limit foaming while providing good wetting and solubilization qualities in the final working solution. Preferred detergents and surfactants include sodium dodecyl sulfate (SDS), lithium lauryl sulfate (LLS), PHOTO-FLO®200 Solution (Eastman Kodak Company, Rochester, N.Y.; Cat. No. 146-4502), saponin, cetyl trimethylammonium bromide (CTAB), ALCONOX® detergent containing 10-30% (w/w) sodium dodecylbenzenesulfonate, 7-13% (w/w) sodium carbonate, 10-30% (w/w) tetrasodium pyrophosphate and 10-13% (w/w) sodium phosphate (Alconox, Inc., White Plains, N.Y.; Cat. No. 1104-1), MICRO-90® cleaning solution containing less than 20% (w/w) glycine, N,N'-1,2-ethanediylbis-(N-(carboxymethyl)-,tetra-sodium salt, less than 20% (w/w) benzenesulfonic acid, dimethyl-, ammonium salt, less than 20% (w/w) benzenesulfonic acid, dodecyl-, cpd. with 2,2',2"-nitrilotris (ethanol), and less than 20% (w/w) poly(oxy-1,2-ethanediyl),alpha-(undecyl)-omega-hydroxy (International Products Corporation, Burlington, N.J.), and polyoxyethylene detergents (e.g., TRITON® X-100). Most preferred are SDS and LLS at a concentration range preferably of from about 0.005% to about 1% (w/v), about 0.005% to about 0.1% (w/v), or about 0.005% to about 0.02% (w/v) in the final working solution.

The wetting agent is included in the formulation to ensure that the deactivating agent makes sufficient contact with the surface being treated and/or to improve the solubility of the deactivating agent and/or other material that may be present on a surface or in a solution to be decontaminated (e.g., nucleic acids, organic substances, oils or films, etc.). Detergents and surfactants are preferred wetting agents because they reduce surface tension and allow for more complete wetting of surfaces with the deactivating agent. Additionally, detergents and surfactants help to solubilize materials to be removed from surfaces or deactivated in a solution. But because detergents and surfactants tend to foam, detergent and surfactant types and concentrations should be selected to limit foaming while providing good wetting and solubilization qualities in the final working solution. Preferred detergents and surfactants include sodium dodecyl sulfate (SDS), lithium lauryl sulfate (LLS), PHOTO-FLO® 200 Solution, saponin, cetyl trimethylammonium bromide (CTAB), Alconox, Micro-90® detergent and polyoxyethylene detergents (e.g., TRITON® X-100). Most preferred are SDS and LLS at a concentration range preferably of from about 0.005% to about 1% (w/v), about 0.005% to about 0.1% (w/v), or about 0.005% to about 0.02% (w/v) in the final working solution.

The formulation further includes the solubilizing agent for helping to maintain the components of the formulation in solution. The solubilizing agent may contain, for example, an organic solvent or an emulsifying agent, such as that found in Fragrance No. 2141-BG, a citrus fragrance available from International Flavors and Fragrances (IFF) of Hazlet, N.J. Fragrances may have the additional advantage of masking the odor of the deactivating agent (e.g., sodium hypochlorite). Organic solvents that may be included in the formulation include benzyl acetate, PS20 and isopropanol. Emulsifying agents that may be included in the formulation include polyoxyethylene sorbitan mono-palmitate (TWEEN® 40), lecithin and ethylene glycol distearate. In some cases, the inventors discovered that the wetting agent was necessary to maintain the solubilizing agent in solution when combined with the corrosion-inhibiting agent and that the solubilizing agent was necessary to maintain the detergent in solution when combined with the corrosion-inhibiting agent. And, when the formulation also include the deactivating agent, all four components remained in solution. When the solubilizing agent is a fragrance, such as IFF Fragrance No. 2415-BG or 2141-BG, the preferred concentration of the solubilizing agent in a final working solution which contains the deactivating agent is in a range from about 0.001% to about 20% (v/v), about 0.001% to about 2% (v/v), or about 0.002% to about 0.2% (v/v). The concentration of the solubilizing agent selected should be such that it has no substantial impact on the activity and stability of the deactivating agent and the corrosion-inhibiting agent.

In a particularly preferred formulation of the present invention, a 6.7× concentrate is prepared having the following formulation: 600 mM sodium bicarbonate, pH 9.3+0.1% SDS+0.05% IFF Fragrance No. 2145-BG. When the formulation further includes a deactivating agent, a particularly preferred formulation is as follows: 0.6% sodium hypochlorite+90 mM sodium bicarbonate, pH 9.3+0.015% SDS+0.0075% IFF Fragrance No. 2145-BG. Of course, the components and concentrations of these preferred formulations can be modified in the manner described herein, without the exercise of undue experimentation, to arrive at alternative formulations that are stable and capable of deactivating nucleic acids on a surface or in a solution while minimizing the potential corrosive effect of the deactivating agent selected.

Based on our discovery that the order in which the agents are combined can be important to preventing the formation of precipitates or an otherwise non-homogenous formulation, a further embodiment of the present invention is directed to a method of making the above-described formulations. This method includes the following ordered steps: (i) separately dissolving solid forms of a corrosion-inhibiting agent and a wetting agent; (ii) combining together the dissolved forms of the corrosion-inhibiting agent and the wetting agent to form a mixture; and (iii) combining together a solubilizing agent and the mixture to form a formulation comprising the corrosion-inhibiting agent, the wetting agent and the solubilizing agent, where the agents of this formulation remain substantially in solution at 22° C. (approximately room temperature). If the solubilizing agent is provided in a solid form, it too may be dissolved prior to combining the solubilizing agent with the mixture. The deactivating agent can then be added to the formulation, where the deactivating agent may be added directly to the formulation or it may be dissolved prior to combining it with the formulation. If water is used to dissolve any of the solid forms of the agents, it is preferably distilled or deionized water. For many of the formulations tested, it was discovered that deviating from the above-ordered steps for combining the agents resulted in the formation of non-homogenous solutions (e.g., the solubilizing agent was first combined with either the corrosion-inhibiting agent or the wetting agent).

For those applications that do not require a wetting agent, we discovered that the deactivating agent and the corrosion-inhibiting agent may be combined without substantially affecting the ability of the deactivating agent to deactivate nucleic acids. Therefore, formulations of the present invention containing corrosive deactivating agents are not required to include a wetting agent and a solubilizing agent.

Another preferred deactivating agent of the present invention comprises hydrogen peroxide and metal ions, such as, for example, copper, cobalt, iron or manganese ions (e.g., cupric sulfate or cupric acetate). For solution-based applications in particular, we found that the metal ions (e.g., copper ions) can be stabilized in a chemical configuration that is active with hydrogen peroxide at deactivating nucleic acids when the deactivating agent further includes piperazine or reagents that contain the piperazine group, such as the buffer HEPES (N-(2-hydroxyethyl)piperazine-N'-(2-ethanesulfonic acid)), acetate, and like compounds and reagents. Surprisingly, we further discovered that piperazine can stimulate the deactivation of nucleic acids in the presence of hydrogen peroxide and copper ions. The hydrogen peroxide of this deactivating agent is preferably present at a concentration range of from about 0.5% to about 30% (w/v), about 1% to about 15% (w/v), or about 1% to about 6% (w/v). Where, for example, copper sulfate is the source of the metal ions, the preferred concentration range of copper sulfate is from about 0.1 mM to about 5 mM, about 0.5 mM to about 2.5 mM, or about 1 mM to about 2.5 mM. And if piperazine is used to stimulate the deactivation of nucleic acids, the preferred concentration range of piperazine is from about 0.5 mM to about 250 mM, about 1 mM to about 200 mM, or about 10 mM to about 100 mM. A preferred formulation of this embodiment comprises 3% hydrogen peroxide+2 mM CuSO$_4$+50 mM piperazine, pH 5.5. This deactivating agent has the advantage of being non-corrosive and odorless.

In a further embodiment, the present invention relates to a method for deactivating nucleic acids suspected of being present on a surface. In this method, a first amount of a first reagent comprising a deactivating agent is applied to the surface. Where warranted by the expected presence of interfering substances (e.g., organic load and/or oily films or residue on the surface), and to ensure adequate deactivation of nucleic acids present on the surface, a second amount of a second reagent comprising a deactivating agent can be applied to the surface. The first and second reagents of this method may be the same or different and one or both of the reagents may comprise one of the formulations described above. In a preferred embodiment, the reagents are removed from the surface, such as by wiping with an absorbent material (e.g., a paper towel or cotton gauze), before the reagents have had an opportunity to completely evaporate. By wiping before the reagents have completely evaporated, nucleic acids that may not have been chemically deactivated by the reagents can be mechanically removed by the absorbent material. Additionally, by wiping with an absorbent material after the first application, other materials solubilized by the first reagent that might consume all or part of the deactivating agent in the second application can be removed. Therefore, in a particularly preferred mode, there is no substantial "soak time" between the applying and removing steps of the preferred embodiment. This means that the delay between application of a reagent to the surface and its removal therefrom is no more than a few minutes, preferably no more than one minute, and, more preferably, the removal of the reagent from the surface immediately follows its application thereto. Also, to avoid all possible sources of contamination, it is recommended that the reagents for deactivating nucleic acids be applied with one gloved hand and that removal of the reagents be performed with another gloved hand.

To reduce the organic load on a surface prior to application of the first reagent, the surface may be pre-treated with an application of a detergent. Additionally, for surface applications, it is recommended that the surface not be cleaned with water following removal of the first or second reagents from the surface, as the water may contain amplifiable nucleic acids or nucleic acids or other chemicals that could interfere with an amplification reaction.

In still another embodiment, the present invention relates to a method for deactivating nucleic acids suspected of being present in one or more conduits using a formulation described above. The conduits may be present, for example, in one or more pipettes or an aspirator manifold. In this method, the formulation containing the deactivating agent is drawn into the one or more conduits, such as by suctioning. The formulation is then dispensed from the one or more conduits. After dispensing the formulation, the one or more conduits may be exposed to a wash solution by drawing the wash solution into the one or more conduits and then dispensing the wash solution from the conduits. The wash solution may be, for example, purified water or a reagent solution and is used to rinse residual amounts of the formulation from the conduits.

In yet another embodiment, the present invention relates to a kit comprising, in one or more receptacles, a formulation as described above for use in deactivating nucleic acids. In one embodiment, if the kit includes a deactivating agent, the deactivating agent is preferably contained in a receptacle separate from one or more receptacles containing the corrosion-inhibiting agent, the wetting agent and/or the solubilizing agent. One or more of the components of the formulation may be provided in a pre-measured amount suitable for making a specific volume of final solution or as a bulk powder. If pre-measured, powder forms of the component or components may be provided in packets or capsules or as tablets to be dissolved in water before being combined with the other components of the formulation. The kit may further include instructions recorded in tangible form (e.g., paper, diskette, CD-ROM, DVD or video cassette) for combining the deactivating agent and the other components of the formulation. The kit may also include one or more reagents for performing a nucleic acid amplification reaction. Such reagents may include one or more enzyme reagents (e.g., an RNA or a DNA polymerase) for use in amplifying a nucleic acid sequence of interest. Enzyme reagents for use in performing a transcription-based amplification, for example, include a reverse transcriptase and an RNA polymerase (e.g., T7 RNA polymerase). Other amplification reagents may also be included, such as, for example, amplification oligonucleotides (e.g., primers, promoter-primers and/or splice templates), nucleotide triphosphates, metal ions and co-factors necessary for enzymatic activity.

BRIEF DESCRIPTION OF THE DRAWINGS

FIGS. 9A-9H show assay results for nucleic acid deactivation by bleach.

FIGS. 11A-11D show PAGE results for nucleic acid deactivation by bleach in the presence of organic load.

FIG. 12 shows PAGE results illustrating scavenging effects of Enzyme Dilution Buffer on DCC and bleach.

DETAILED DESCRIPTION

The present invention is directed in part to formulations, methods and kits which are useful for deactivating nucleic acids. These formulations, methods and kits are described above and in the examples and claims which follow. In addition, the examples describe screening methods for selecting formulations of the present invention which are useful for deactivating nucleic acids on work surfaces, laboratory equipment and/or in solution, or which could be used as, for example, disinfectants. Such formulations may also be useful for deactivating biological molecules, like proteins and lipids. The examples further consider the effect of a number of exemplary formulations in both pre- and post-amplification applications.

EXAMPLES

The examples set forth below illustrate but do not limit the invention.

Example 1

Effect of Various Concentrations of Bleach on Visualization of DNA by Gel Electrophoresis An experiment was conducted in which a 71-mer DNA oligonucleotide was reacted with various concentrations of ULTRA CLOROX® BLEACH (The Clorox Company, Oakland, Calif.) at a concentration of 6.15% (w/v) sodium hypochlorite, and the reaction products were analyzed using polyacrylamide gel electrophoresis (PAGE). Ten samples were prepared by mixing 2 μL of the DNA oligonucleotide, at a concentration of 173 μg/mL, with distilled water in sample vials before adding varying concentrations of bleach to bring the total volume of each sample to 20 μL. The samples were mixed by vortexing for about 10 seconds and then provided with 20 μL of a 2X TBE-Urea sample buffer containing 180 mM Tris base, 180 mM boric acid, 4 mM ethylenediaminetetraacetic acid (EDTA), pH 8.0 (Invitrogen Corporation, Carlsbad, Calif.; Cat. No. LC 6876), bringing the total volume of each sample to 40 μL. The samples were again mixed by vortexing for about 10 seconds. Final bleach concentrations in the samples ranged from 0 to 50% bleach, as set forth in Table 1 below. A 10 μL aliquot of each sample was loaded into one of the 10 lanes of a 10% polyacrylamide TBE-Urea gel, and the gel was run for 40 minutes at 180 V. When the run was completed, the gel was removed from its cast, contacted with 100 mL of a SYBR® Green I nucleic acid gel stain (Molecular Probes, Eugene OR; Cat. No. 57563) diluted 1/10,000 with distilled water, and mixed at 10 rpm for 30 minutes. After staining, the gel was photographed using a CHEMIIMAGER™ System 4400 (Alpha Innotech Corporation, San Leandro, CA). The separated products stained on a gel are commonly referred to as bands. A copy of the resulting electrophoretogram is presented in FIG. 1.

| Lane | % Bleach |
|---|---|
| 1 | 0 |
| 2 | 0.01 |
| 3 | 0.03 |
| 4 | 0.1 |
| 5 | 0.3 |
| 6 | 1 |
| 7 | 3 |
| 8 | 10 |
| 9 | 20 |
| 10 | 50 |

Figure 1:
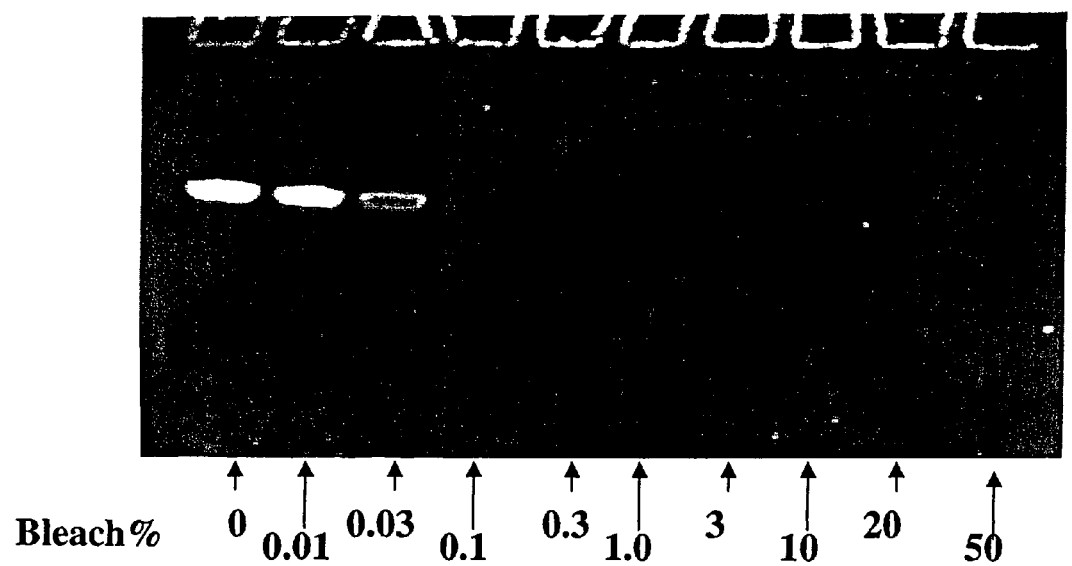
FIG. 1 is an electrophoretogram showing the results of a fixed amount of a 71-mer, single-stranded DNA oligonucleotide reacted with varying concentrations of bleach following polyacrylamide gel electrophoresis (PAGE).

From the results illustrated in the electrophoretogram of FIG. 1, it can be seen that the last visible band appears in lane 3. These results suggest that between 0.03% (0.25 mM) and 0.1% (0.82 mM) sodium hypochlorite was needed to substantially alter the DNA present in the samples. From the DNA oligonucleotide concentration indicated above, it was determined that the nucleotide concentration in the samples was 0.52 M. Thus, the sodium hypochlorite to nucleotide molar ratio was approximately 1:1, suggesting that about one mole sodium hypochlorite reacted with about one mole nucleotide. Another similar experiment comparing incubation times of 0 to 20 minutes showed no changes in the appearance of oligonucleotide bands over the time course of hypochlorite incubation, suggesting the reaction rate is rapid.

Example 2

Figure 2:
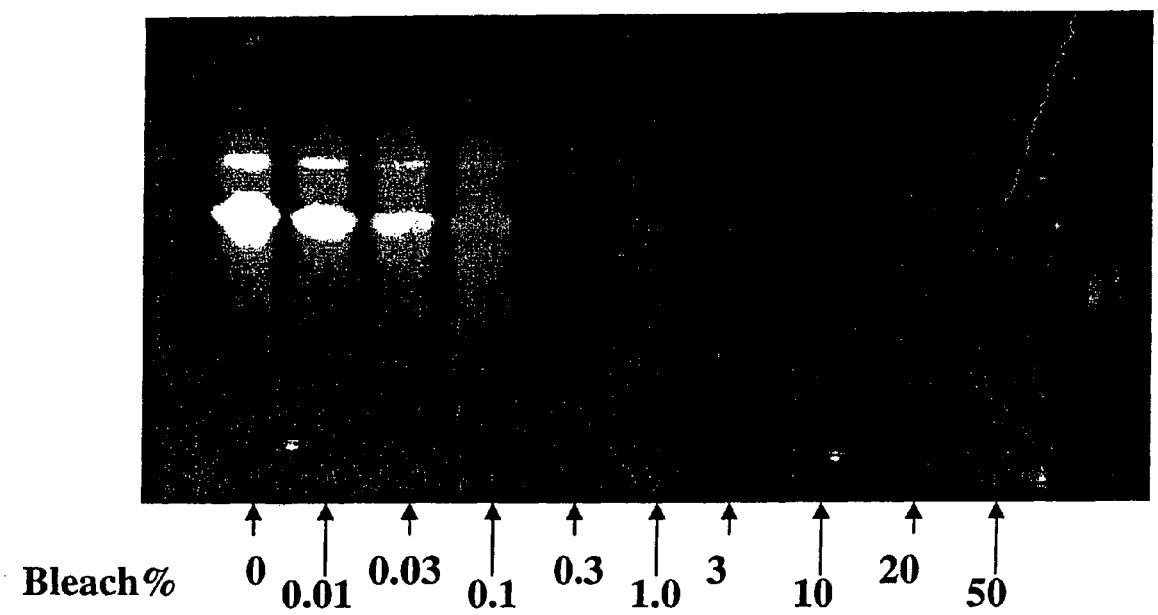
FIG. 2 is an electrophoretogram showing the results of a fixed amount of a 60-mer, single-stranded DNA/RNA chimera oligonucleotide reacted with varying concentrations of bleach following PAGE. The RNA consisted of 2'-O-methyl ribonucleotides.

Effect of Various Concentrations of Bleach on Visualization of a DNA/RNA Chimera by Gel Electrophoresis The experiment of Example 1 was repeated, substituting a 60-mer DNA/RNA chimeric oligonucleotide at a concentration of 200 μg/ml for the DNA oligonucleotide of that experiment. The RNA of the chimera consisted of 2'-O-methyl ribonucleotides. A copy of the resulting electrophoretogram appears in FIG. 2 and shows that most of the oligonucleotide band disappeared at 0.1% bleach, again about a 1:1 molar ratio of sodium hypochlorite to nucleoside. The concentrations of bleach used in the various lanes of the gel of this experiment are the same as those described in the experiment of Example 1.

Example 3

Effect of Various Concentrations of Bleach on Visualization of DNA by Gel Electrophoresis Dichloroisocyanuric acid, sodium salt (DCC) (Sigma-Aldrich, Milwaukee, WI; Prod. No. 21,892-8) and ULTRA CLOROX® BLEACH (6.15% (w/v) sodium hypochlorite) were examined at varying available chlorine concentrations in this experiment for their comparative abilities to react with nucleic acid. The chlorine concentrations tested are set forth in Table 2 below. In all other aspects, including the use of the 71-mer DNA oligonucleotide, this experiment was identical to the experiment detailed in Example 1.

| Lane | Chlorine (mM) |
|---|---|
| 1 | 0 |
| 2 | 0.8 |
| 3 | 0.24 |
| 4 | 0.8 |
| 5 | 2.4 |
| 6 | 8 |
| 7 | 24 |

-continued

| Lane | Chlorine (mM) |
|------|---------------|
| 8 | 80 |
| 9 | 160 |
| 10 | 400 |

Figure 3:
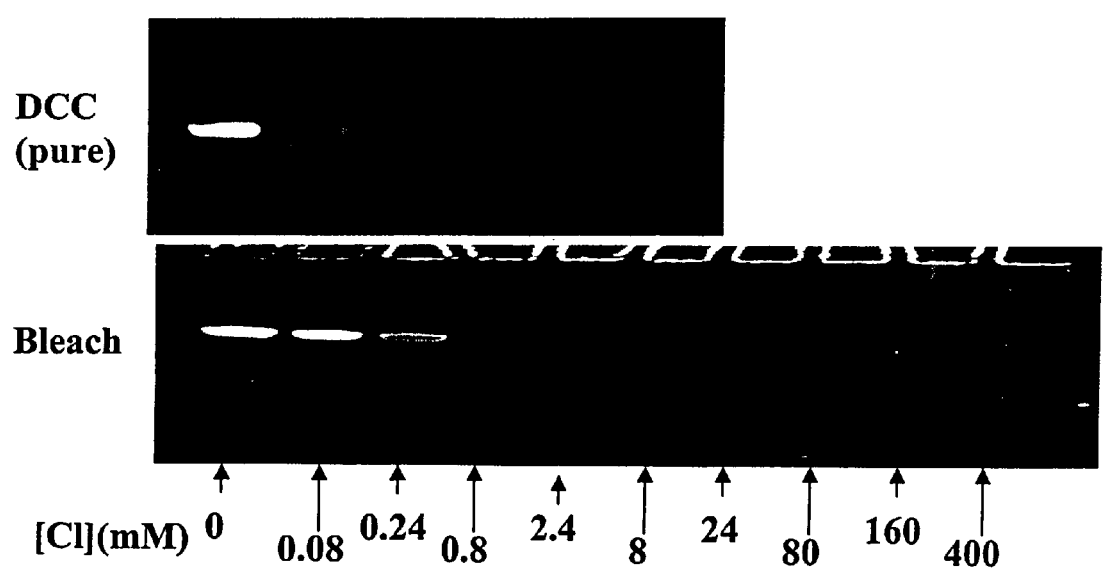
FIG. 3 is comprised of two electrophoretograms showing the results of a fixed amount of a 71-mer, single-stranded DNA oligonucleotide reacted with varying concentrations of dichloroisocyanurate or bleach, respectively, following PAGE.

The results of this experiment are illustrated in FIG. 3 and indicate that pure DCC causes the disappearance of the DNA band at lower concentrations than the bleach solution at the same chlorine concentration.

Example 4

Effect if Various Concentrations of Hydrogen Peroxide and Hydrogen Peroxide Plus Cupric Sulfate on Visualization of DNA by Gel Electrophoresis In this experiment, a 71-mer DNA oligonucleotide present at a concentration of 53 µg/mL was reacted with various concentrations of 30% (w/v) hydrogen peroxide (Fisher Scientific, Tustin, Calif.; Cat. No. BP2633-500) and 30% (w/v) hydrogen peroxide plus cupric sulfate (Sigma-Aldrich, Milwaukee, WI; Prod. No. 45,165-7), and the reaction products were analyzed using polyacrylamide gel electrophoresis (PAGE). Ten samples were prepared in the manner indicated in Table 3 below, with the DNA and water being combined prior to adding 30% (w/v) hydrogen peroxide (8.8 M) and/or 1 mM cupric sulfate. The remaining procedural details of this experiment are the same as those set forth in Example 1. The concentration of peroxide in each lane is set forth in Table 4 below.

TABLE 3

Sample Mixtures

| | | Components (µL) | | | |
|---|---|---|---|---|---|
| | | DNA | CuSO$_4$ | H$_2$O$_2$ | H$_2$O |
| Sample | 1 | 2 | 0 | 0 | 18 |
| Number | 2 | 2 | 2 | 0 | 16 |
| | 3 | 2 | 0 | 16 | 2 |
| | 4 | 2 | 2 | 0.33 | 15.7 |
| | 5 | 2 | 2 | 1 | 15 |
| | 6 | 2 | 2 | 2 | 14 |
| | 7 | 2 | 2 | 4 | 12 |
| | 8 | 2 | 2 | 8 | 8 |
| | 9 | 2 | 2 | 12 | 4 |
| | 10 | 2 | 2 | 16 | 0 |

TABLE 4

Hydrogen Peroxide Concentrations

| Lane | % H$_2$O$_2$ (w/v) |
|------|--------------------|
| 1 | 0 |
| 2 | 0 |
| 3 | 24 |
| 4 | 0.5 |
| 5 | 1.5 |
| 6 | 3 |
| 7 | 6 |
| 8 | 12 |
| 9 | 18 |
| 10 | 24 |

Figure 4:
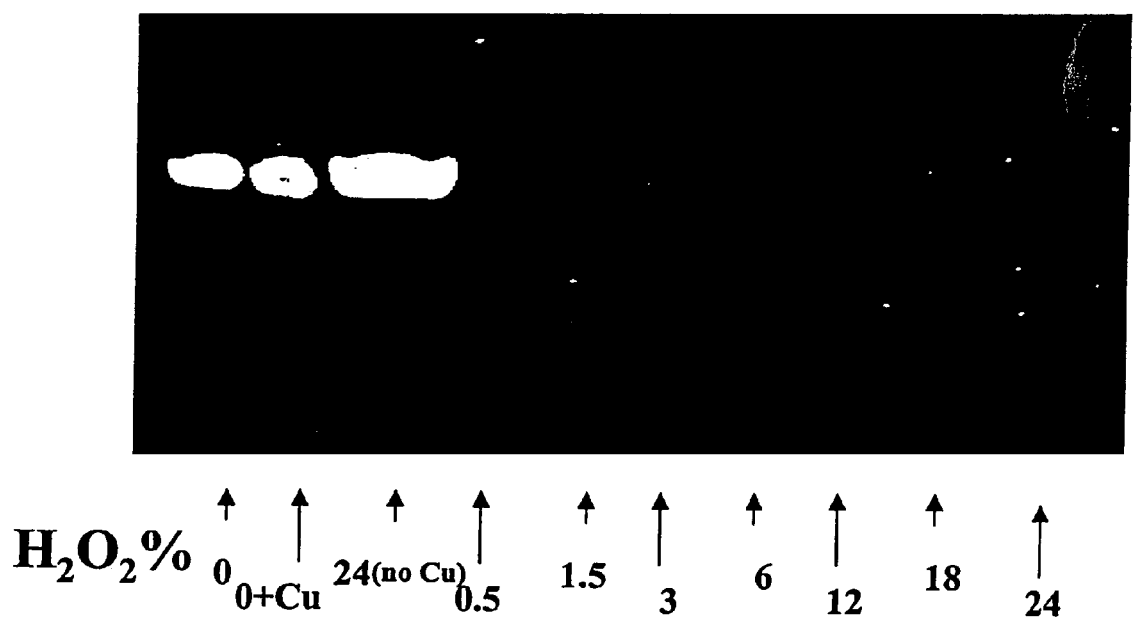
FIG. 4 is an electrophoretogram showing the results of a fixed amount of a 71-mer, DNA oligonucleotide reacted with varying concentrations of hydrogen peroxide alone or in combination with a fixed concentration cupric sulfate following PAGE.

The resulting electrophoretogram appears in FIG. 4 and indicates that the peroxide and the cupric sulfate do not independently cause the disappearance of the DNA oligonucleotide bands at the indicated concentrations. However, the electrophoretogram does appear to demonstrate that mixtures of peroxide and cupric sulfate are effective at causing the disappearance of the DNA oligonucleotide bands at all concentrations tested. This suggests that the cupric sulfate may function as a catalyst for the peroxide in the degradation of nucleic acids.

Example 5

Effect of Various Concentrations of Hydrogen Peroxide in the Presence of Cupric Sulfate on Visualization of DNA by Gel Electrophoresis The experiment of Example 4 was repeated using lower concentrations of the hydrogen peroxide compound and 100 µM cupric sulfate in all lanes of the gel. The final concentration of peroxide in each lane of the gel is set forth in Table 5 below.

TABLE 5

Peroxide Concentrations

| Lane | % H$_2$O$_2$ (w/v) |
|------|--------------------|
| 1 | 0 |
| 2 | 0.0005 |
| 3 | 0.005 |
| 4 | 0.01 |
| 5 | 0.02 |
| 6 | 0.04 |
| 7 | 0.1 |
| 8 | 0.2 |
| 9 | 0.4 |
| 10 | 1 |

Figure 5:
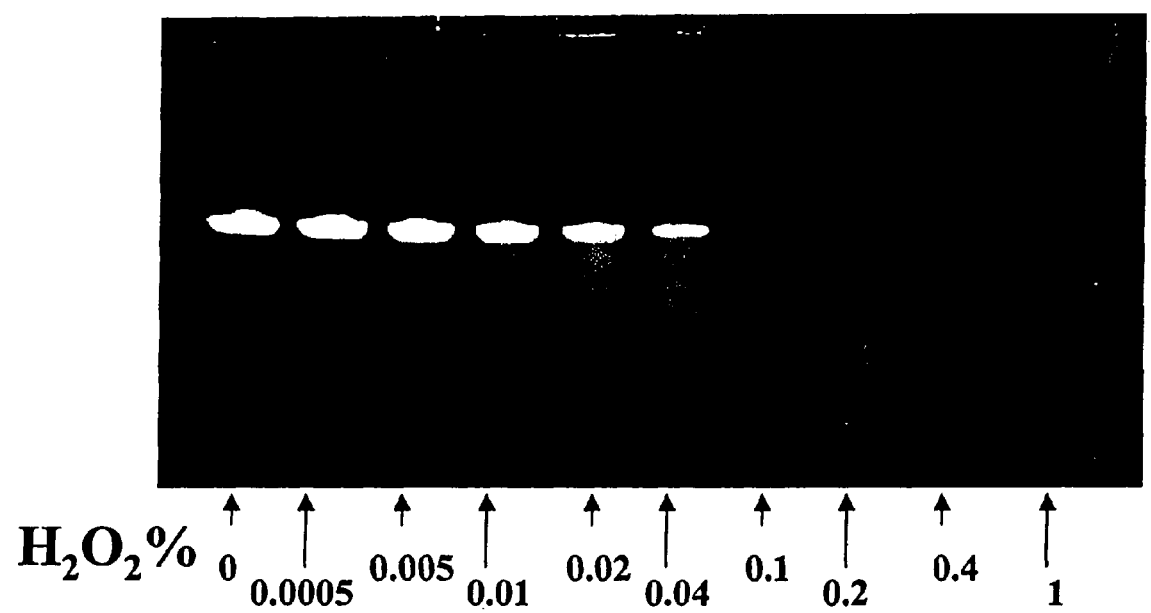
FIG. 5 is an electrophoretogram showing the results of a fixed amount of a 71-mer, DNA oligonucleotide reacted with varying concentrations of hydrogen peroxide and a fixed amount of cupric sulfate following PAGE.

A copy of the resulting electrophoretogram appears in FIG. 5 and shows no band at 0.2% (w/v) hydrogen peroxide and only a faint band at 0.1% (w/v) hydrogen peroxide.

Example 6

Effect of NALC Upon Reaction of Bleach with DNA

Bleach is known to react with a variety of organic materials. These materials may thus interfere with the deactivation of nucleic acids by reacting with and consuming the bleach. The presence of these organic materials thus constitutes an "organic load" that must be compensated for by the presence of sufficient bleach to react with both the DNA and the organic materials. In this experiment, the scavenging effect of N-acetyl-L-cysteine (NALC), an organic load compound (i.e., a compound that may be expected to consume bleach), was examined in the presence of varying concentrations of ULTRA CLOROX® BLEACH. NALC is a reducing agent found in some enzyme reagents intended for use in amplification reactions. Two sets of 10 samples were prepared in this experiment, each sample containing 2 µL of a 71-mer DNA oligonucleotide at a concentration of 173 µg/mL. The first set of samples contained no NALC, while each sample of the second set of samples contained 16 µL NALC at a concentration of 11.4 mg/mL. The samples were prepared by first providing the DNA and NALC (if any) to sample vials and mixing the samples containing NALC by vortexing for about 10 seconds. The bleach was then added to both sets of samples at varying concentrations, along with distilled water, to bring the total volume of each sample to 20 µL. The samples were mixed by vortexing for about 10 seconds before adding 20 μL of a 2X TBE-Urea sample buffer (Invitrogen Corporation; Cat. No. LC 6876), bringing the total volume of each sample to 40 μL. The samples were again mixed by vortexing for about 10 seconds. Final bleach concentrations in the samples ranged from 0% to 50% bleach, as set forth in Table 6 below. A 10 μL aliquot of each sample was loaded into one of 10 lanes of a 10% polyacrylamide TBE-Urea gel, a separate gel being provided for each of the two sets of samples, and the gels were run for 40 minutes at 180 V. When the runs were completed, the gels were removed from their casts, contacted with 100 mL of a SYBR® Green I nucleic acid gel stain (Molecular Probes; Cat. No. S7563) diluted 1/10,000 with distilled water, and mixed at 10 rpm for 30 minutes. After staining, the gels were photographed using a ChemiImager™ System 4400, and a copy of the resulting electrophoretogram is presented in FIG. 6.

| Lane | % Bleach (v/v) |
|---|---|
| 1 | 0 |
| 2 | 0.01 |
| 3 | 0.03 |
| 4 | 0.1 |
| 5 | 0.3 |
| 6 | 1 |
| 7 | 3 |
| 8 | 10 |
| 9 | 20 |
| 10 | 50 |

Figure 6:
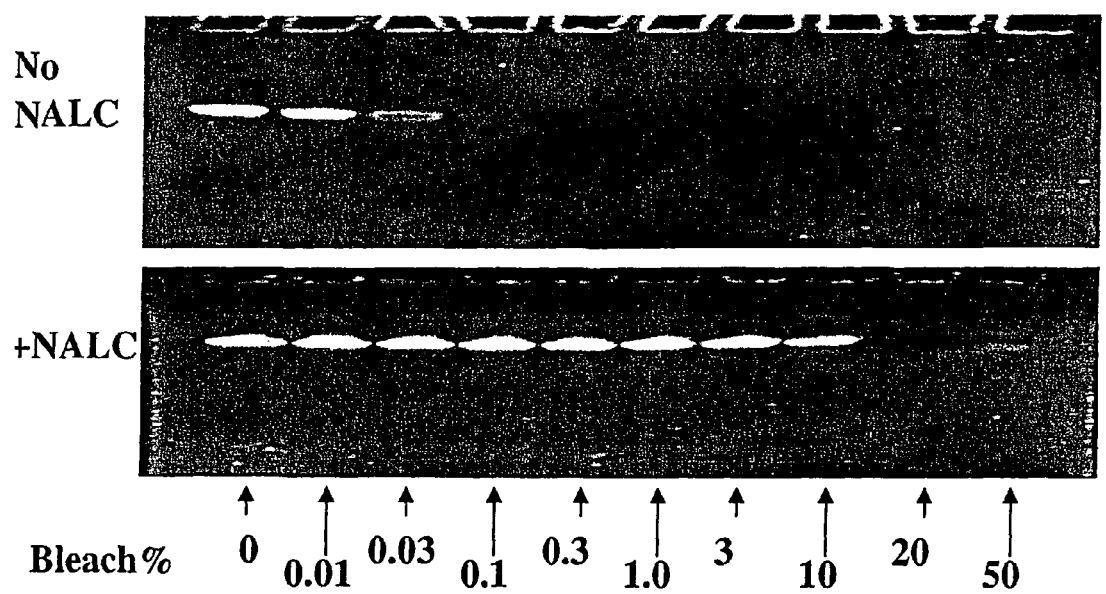
FIG. 6 is comprised of two electrophoretograms showing the results of a fixed amount of a 71-mer, single-stranded DNA oligonucleotide reacted with varying concentrations of bleach in the presence or absence of NALC following PAGE.

From the results illustrated in the electrophoretograms of FIG. 6, it can be seen that the last clearly visible band appears in lane 3 (0.03% (v/v) bleach) of the gel having samples containing no NALC and in lane 8 (10% (v/v) bleach) of the gel having samples containing NALC. These results indicate that the concentration of bleach needed to cause the disappearance of the DNA bands is affected by the presence of NALC, which likely competes with the DNA for reaction with bleach.

Example 7

Effect of NALC and Human Serum Upon Reaction of Hydrogen Peroxide and Cupric Sulfate Mixture with DNA In this experiment, the effect of NALC and human serum upon the reaction of various concentrations of hydrogen peroxide and cupric sulfate with DNA was examined. A set of 11 samples was prepared, each sample containing 2 μL of a 71-mer DNA oligonucleotide at a concentration of 53 μg/mL. Other components of the samples included 100 μM cupric sulfate, 30% (w/v) hydrogen peroxide, and NALC at a concentration of 11.4 mg/mL. The amount of each component in the sample vials is set forth in Table 7 below. The samples were prepared by combining all sample components, except the hydrogen peroxide, in sample vials and mixing by vortexing for about 10 seconds. After mixing, the hydrogen peroxide was added to the samples at varying concentrations, bringing the total volume of sample 1 to 20 μL and samples 2-11 to 22 μL and giving the final concentrations indicated in Table 8 below. The samples were again mixed by vortexing for about 10 seconds before adding 20 μL of a 2×TBE-Urea sample buffer (Invitrogen Corporation; Cat. No. LC 6876), bringing the total volume of sample 1 to 40 μL and samples 2-11 to 42 μL. The remainder of the procedure and sources of the reagents were identical to that set forth in Example 6 above. A copy of the resulting electrophoretogram is presented in FIG. 7.

TABLE 7

Sample Mixtures

| | | Components (μL) | | | | | |
|---|---|---|---|---|---|---|---|
| | | DNA | CuSO$_4$ | H$_2$O$_2$ | NALC | Human Serum | H$_2$O |
| Sample Number | 1 | 2 | 0 | 0 | 0 | 0 | 18 |
| | 2 | 2 | 2 | 1 | 0 | 0 | 17 |
| | 3 | 2 | 2 | 4 | 0 | 0 | 14 |
| | 4 | 2 | 2 | 12 | 0 | 0 | 6 |
| | 5 | 2 | 2 | 1 | 4 | 0 | 13 |
| | 6 | 2 | 2 | 4 | 4 | 0 | 10 |
| | 7 | 2 | 2 | 12 | 4 | 0 | 2 |
| | 8 | 2 | 2 | 0 | 0 | 4 | 14 |
| | 9 | 2 | 2 | 1 | 0 | 4 | 13 |
| | 10 | 2 | 2 | 4 | 0 | 4 | 10 |
| | 11 | 2 | 2 | 12 | 0 | 4 | 2 |

TABLE 8

Peroxide Concentrations

| Lane | % H$_2$O$_2$ (w/v) |
|---|---|
| 1 | 0 |
| 2 | 1.36 |
| 3 | 5.45 |
| 4 | 16.36 |
| 5 | 1.36 |
| 6 | 5.45 |
| 7 | 16.36 |
| 8 | 0 |
| 9 | 1.36 |
| 10 | 5.45 |
| 11 | 16.36 |

Figure 7:
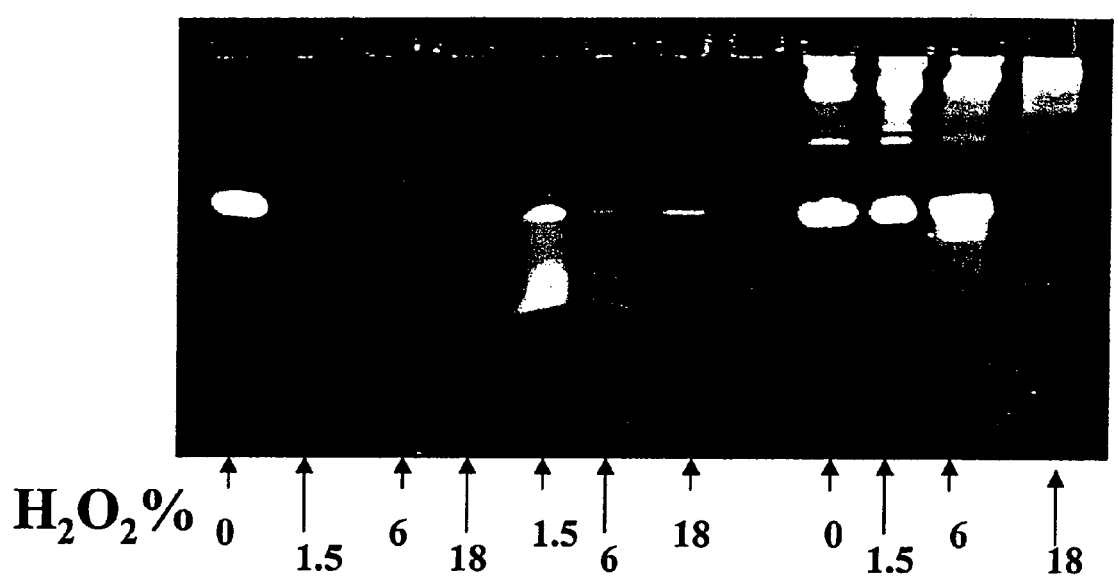
FIG. 7 is an electrophoretogram showing the results of a fixed amount of a 71-mer, single-stranded DNA oligonucleotide reacted with varying concentrations of hydrogen peroxide and a fixed amount of cupric sulfate in the presence or absence of a fixed amount of NALC or human serum following PAGE.

The results illustrated in the electrophoretograms of FIG. 7 show that NALC and serum interfere with the reaction of the hydrogen peroxide and cupric sulfate mixture with DNA. Thus, these results demonstrate that the amount of hydrogen peroxide needed to cause the disappearance of the DNA bands is affected by the presence of NALC and human serum, which likely compete with the DNA for reaction with bleach.

Example 8

Nucleic Acids with Bleach in a Pure System

This experiment was conducted to evaluate the ability of various bleach concentrations to deactivate purified ribosomal RNA derived from *Neisseria gonorrhoeae* ("target") in a pure system. Eight sample tubes were initially set up to contain 4 μL of target-containing water and 4 μL of bleach in the concentrations indicated in Table 9. For sample tubes 6 and 8, 4 μL of water was used in place of a bleach solution). The bleach used in this experiment was Ultra Chlorox® Bleach (6.15% (w/v) sodium hypochlorite). After set up, the contents of the sample tubes were incubated for 5 minutes at room temperature.

TABLE 9

Bleach Concentrations

| Sample Tube | Initial Target Concentration (copies/μL) | Initial Bleach Concentration % (v/v) | Final Bleach Concentrations % (v/v) |
|---|---|---|---|
| 1 | $10^8$ | 40 | 20 |
| 2 |  | 10 | 5 |
| 3 |  | 4 | 2 |
| 4 |  | 1 | 0.5 |
| 5 |  | 0.4 | 0.2 |
| 6 |  | 0 | 0 |
| 7 | 0 | 40 | 20 |
| 8 |  | 0 | 0 |

Following the room temperature incubation, 392 μL of water (chilled on ice) was added to each sample tube. The samples then were analyzed by a real-time Transcription-Mediated Amplification (TMA) assay. In the assay, amplification reaction mixtures were prepared by combining a 4 μL aliquot from each sample tube with 300 μL of an Amplification Reagent (44.1 mM HEPES, 2.82% (w/v) trehalose, 33.0 mM KCl, 9.41 mM rATP, 1.76 RCTP, 11.76 rGTP, 1.76 mM UTP, 0.47 mM dATP, 0.47 mM dCTP, 0.47 mM dGTP, 0.47 mM dTTP, 30.6 mM $MgCl_2$, 0.30% (v/v) ethanol, 0.1% (w/v) methyl paraben, 0.02% (w/v) propyl paraben, and 0.003% (w/v) phenol red) at pH 7.7 and spiked with 25.6 pmol of a T7 promoter-primer and 20.0 pmol of a non-T7 primer for amplifying a region of the target following a Transcription-Mediated Amplification (TMA) procedure (see Kacian et al., U.S. Pat. No. 5,399,491) and 80 pmol of a molecular beacon probe for detecting the resulting amplicon in real-time (see Tyagi et al., "Detectably Labeled Dual Conformation Oligonucleotide Probes, Assays and Kits," U.S. Pat. No. 5,925,517). The probes and primers of this experiment were synthesized on an Expedite™ 8909 Nucleic Acid Synthesizer (Applied Biosystems, Foster City, Calif.) using standard phosphoramidite chemistry. See, e.g., Caruthers et al., Methods in Enzymology, 154:287 (1987). The molecular beacon probes were synthesized to include interacting CyTM5 and BHQTM dyes using Cy5-CE phosphoramidite (Glen Research Corporation, Sterling, Va.; Cat. No. 10-5915-90) and 3'-BHQ-2 Glycolate CPG (BioSearch Technologies, Inc., Novato, Calif.; Cat. No. CG5-5042G-1).

Amplification reaction mixtures were then set up in a 96-well, MICROTITER® plate (Thermo Labsystems, Helsinki, Finland; Cat. No. 9502887) in replicates of three, each well containing 75 μL of a light mineral oil and 75 μL of the amplification reaction mixture. The plates were covered with ThermalSeal sealing film (Sigma-Aldrich Co., St. Louis, Mo.; Product No. Z36,967-5) and incubated in a Solo HT Microplate Incubator (Thermo Electron Corporation; Milford, Mass.) for 15 minutes at 62°C. to permit hybridization of the promoter-primer to the target, followed by a second 15 minute incubation in the Solo HT Microplate Incubator at 42°C. After incubating the contents of the plate, a multi-channel pipettor was used to add 25 μL of an Enzyme Reagent (50 mM N-acetyl-L-cysteine (NALC), 58 mM HEPES, 3.03% (w/v) trehalose, 10% TRITON® X-100 detergent, 1.04 mM EDTA, 20% (v/v) glycerol, 120 mM KCl, 120 RTU/μL Moloney murine leukemia virus ("MMLV") reverse transcriptase, and 80 U/μL T7 RNA polymerase, where "one unit" of activity is defined as the synthesis and release of 5.75 fmol cDNA in 15 minutes at 37°C. for MMLV reverse transcriptase, and the production of 5.0 fmol RNA transcript in 20 minutes at 37 °C. for T7 RNA polymerase) at pH 7.0 to each sample. Immediately after each set of Enzyme Reagent additions, the contents of the reaction wells were mixed by stirring with the corresponding pipette tips held by the pipettor. To measure the formation of amplicon in real-time, the plate was transferred to a Fluoroskan Ascent microplate fluorometer (Thermo Electron Corporation; Product No. 5210470) and incubated for 60 minutes at 42°C. Fluorescence from the reaction wells was measured in 30 second increments using a 639 nm excitation filter and 671 nm emission filter.

Figure 8:
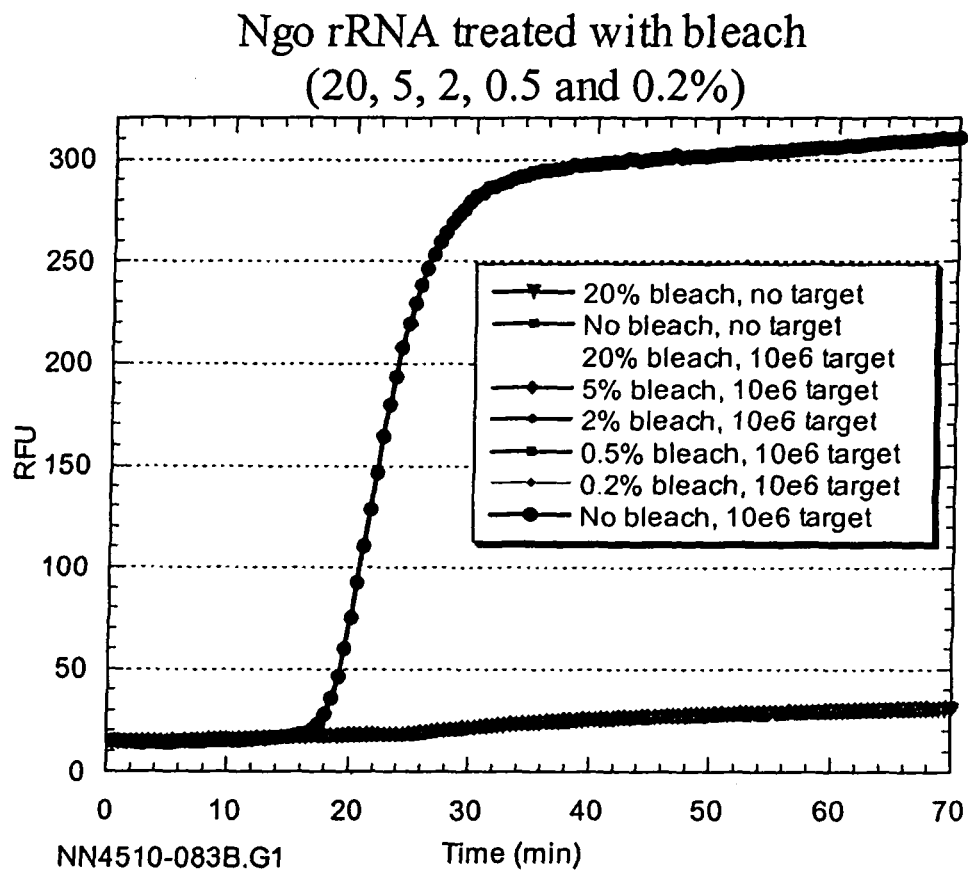
FIG. 8 is a graph showing the results of a real-time amplification after reacting a target nucleic acid with varying concentrations of bleach in a pure system.

The results of this experiment are reported in the graph of FIG. 8, which plots relative fluorescent units (RFU) on the y-axis and time in minutes on the x-axis. The results show that even at 0.2% bleach, the lowest bleach concentration tested, the target nucleic acid in this pure system was deactivated, such that it could not be detectably amplified. Detectable amplification in this experiment would have been RFU value more than two-fold the background RFU value (sample tube 8) in a 60 minute amplification period.

Example 9

Further Characterization of Nucleic Acid Deactivation in a Pure Bleach System Several formulations were tested for efficacy in deactivating nucleic acids using multiple assays.

A. Real-Time TMA Results

Figure 9A:
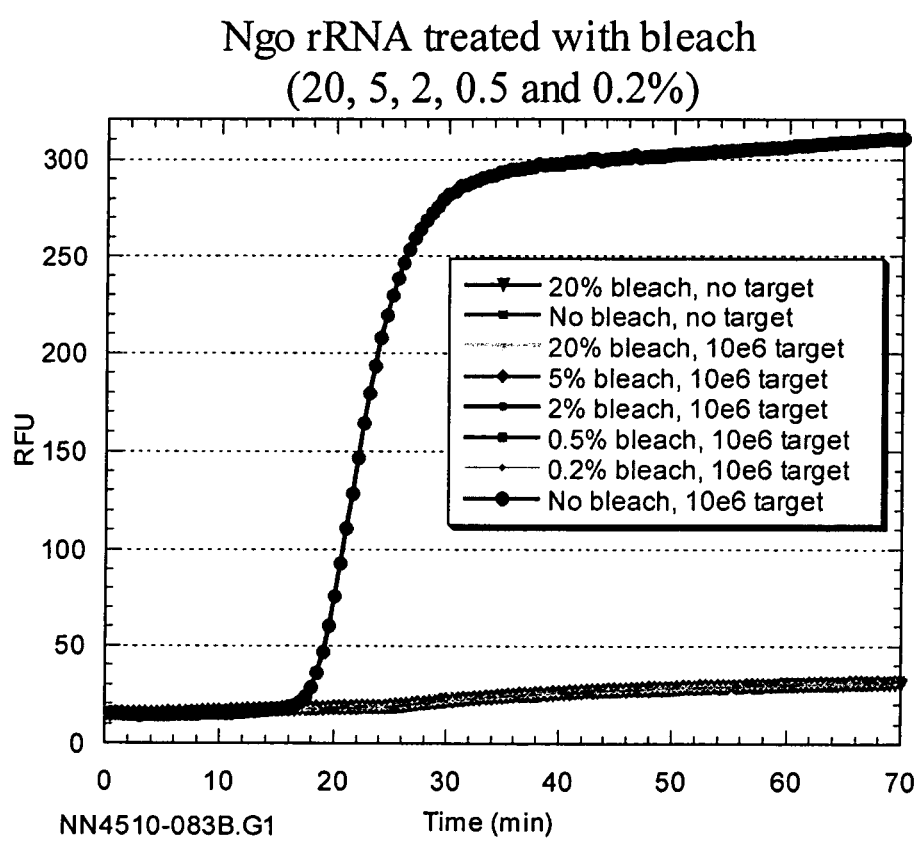

*Neisseria gonorrhoaea* (Ngo) ribosomal RNA (rRNA) was reacted with 0-20% commercial bleach, where the lowest bleach concentration was 0.2%, in a pure system and reaction products were analyzed by real-time TMA assays (see Example 8). Even at the lowest bleach concentration the rRNA was inactivated within the limits of sensitivity of the real-time assay (FIG. 9A).

Figure 9B:
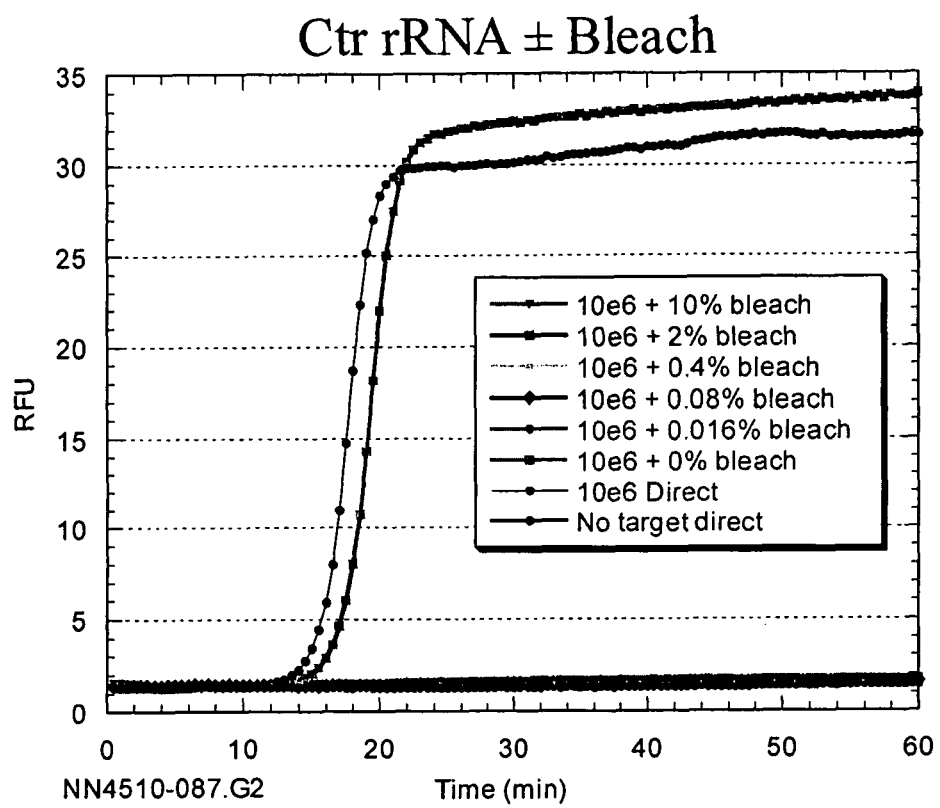
Figure 10A:
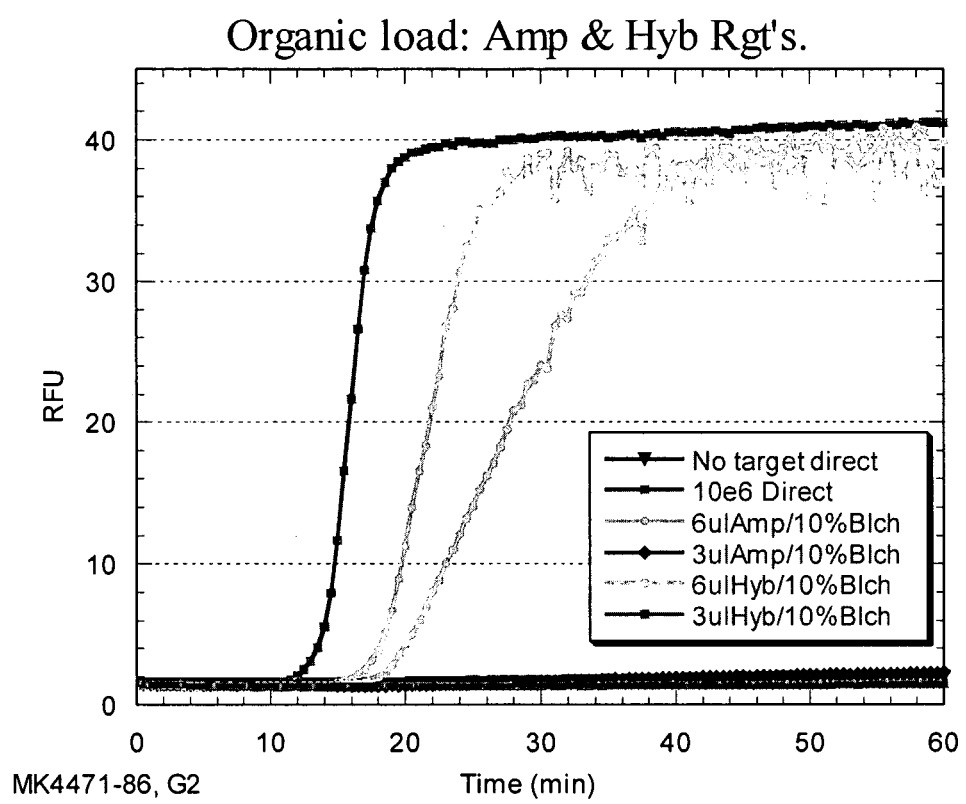
FIGS. 10A-10F show real-time transcription-mediated amplification (TMA) results for nucleic acid deactivation by bleach in the presence of organic load.
Figure 10B:
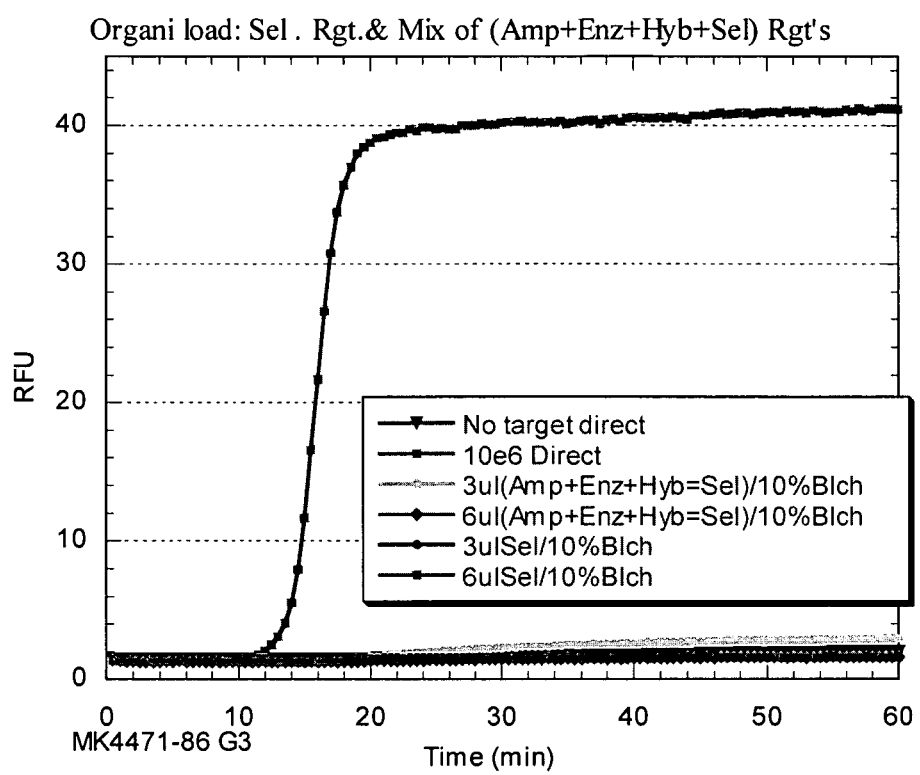
Figure 10C:
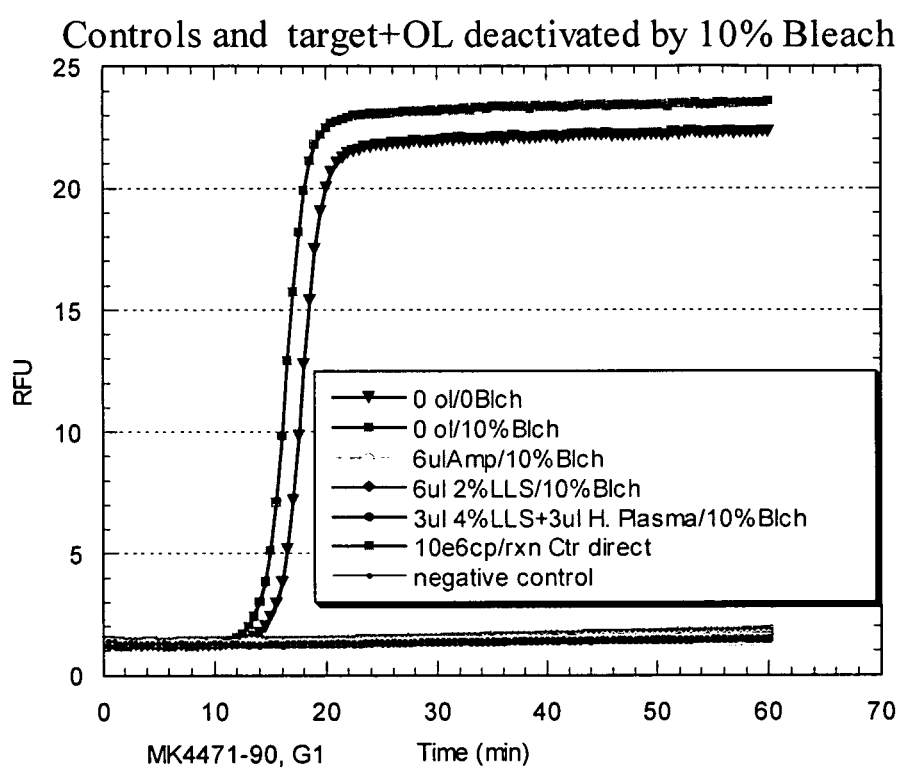
Figure 10D:
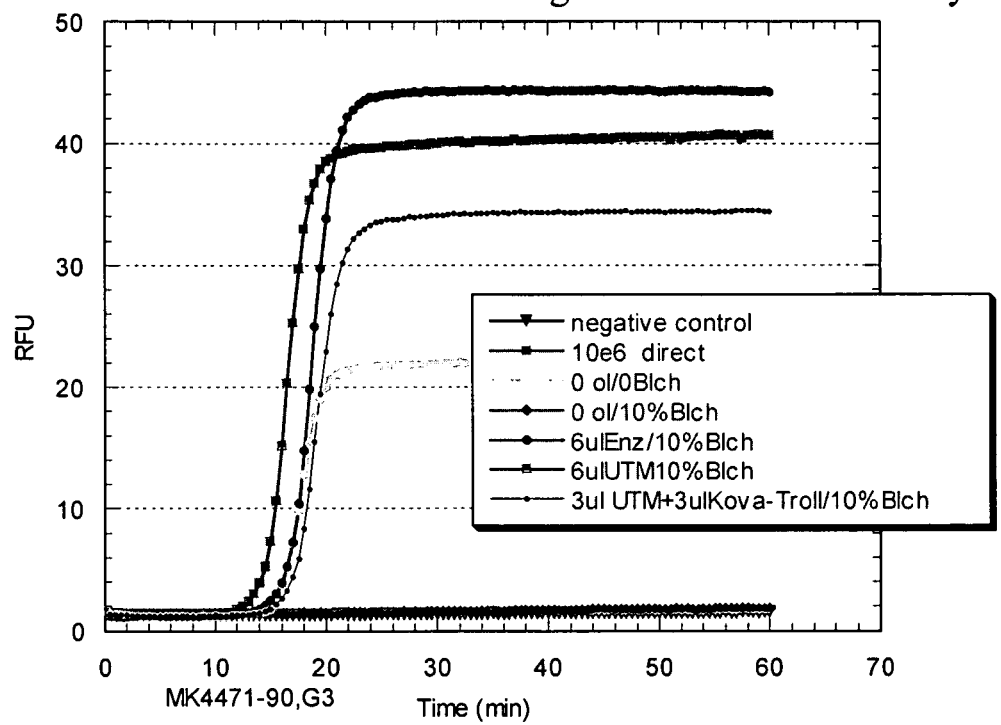
Figure 10E:
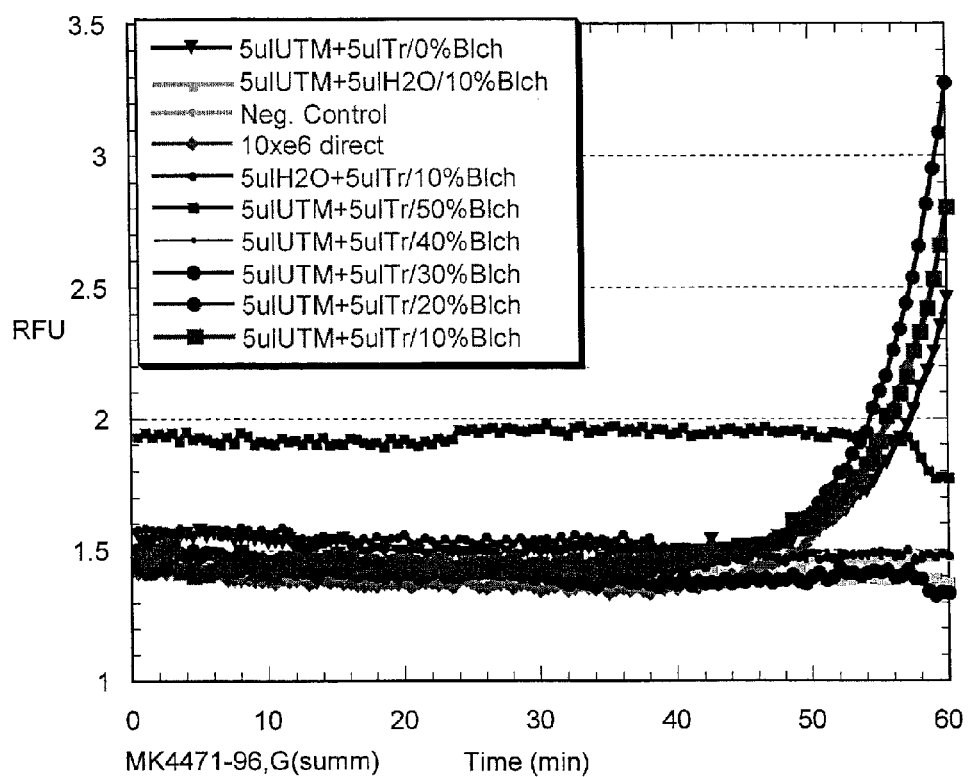
Figure 10F:
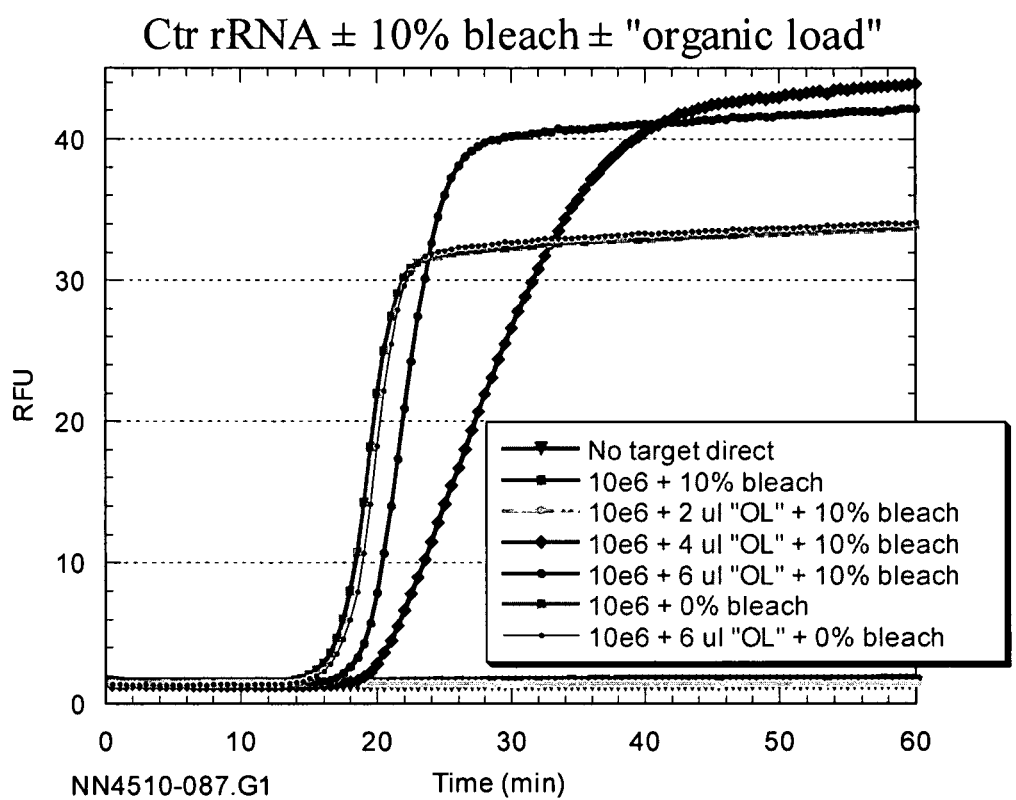

*Chlamydia trachomatis* (Ctr) rRNA also was reacted with 0-20% bleach, where the lowest bleach concentration was 0.016%, in a pure system and reaction products were analyzed by real-time TMA assays. The lowest bleach concentration also inactivated the rRNA (FIG. 9B).

B. Capillary Electrophoresis Results

Ribosomal RNA was reacted with bleach in solution and products were analyzed by capillary electrophoresis. An Agilent 2100 Bioanalyzer was utilized to characterize nucleic acids exposed to deactivation solutions. In a 10 μL total reaction, the following were added (in order): (a) Milli-Q $H_2O$ or buffer, (b) an indicated amount of reagent (e.g., —OCl from bleach or $H_2O_2$), and (c) 0 nM (blank) or 150 nM (718 μM =470 ng/μL nt) *Mycobacterium tuberculosis* (Mtb) rRNA or 15 nM (71.8 μM =47.0 ng/μL nt) Mtb rRNA. The reactants were incubated for 10 min at room temperature (ca. 23°C.), and 90 μL 1 mM sodium ascorbate (900 μM final) then was added. As in the LABCHIP® protocol (Agilent Technologies, Inc.; Palo Alto, Calif.), the RNA ladder was denatured at 70°C. for 2 min, and then 1 μL of each reaction was loaded into wells on RNA 6000 Nano LABCHIP® or Pico LABCHIP® (Agilent Technologies, Inc.; Palo Alto, Calif.) containing 5 μL sample buffer. The components were mixed and the assay Prokaryote Total RNA was run in the Bio Sizing program (Agilent Technologies, Inc.; Palo Alto, Calif.).

Results from the capillary electrophoresis analysis showed a 1:1 ratio of hypochlorite-to-rRNA nucleotide substantially eliminated rRNA peaks (FIG. 9C to 9F). A time course of the reaction between rRNA and bleach also was performed (FIGS. 9G and 9H). The reaction with both the 16S and 23S subunits is very fast, essentially over within 1 min, with pseudo-first order rate constants for the decay of rRNA approaching at least 0.02 $s^{-1}$.

C. Conclusions

Reaction of bleach (hypochlorite) with nucleic acids in a pure system was rapid and essentially complete at a 1:1 ratio of hypochlorite to nucleoside. These data suggested that any observed lack of decontamination of nucleic acids in the laboratory using bleach was not due to an inherently slow reaction of hypochlorite with the nucleic acids or the need for a high molar excess of bleach over the nucleic acids.

Example 10

Further Characterization of Nucleic Acid Deactivation by Bleach in the Presence of Organic Load Effects of N-acetyl-L-cysteine (NALC), an organic load material, on the reaction between bleach and oligonucleotides were characterized by PAGE in Example 6. Presented hereafter is a characterization of the effects of NALC and other organic load materials on the reaction between oligonucleotides and bleach using PAGE and other characterization methods.

A. Real-Time TMA Results

Ribosomal RNA was reacted with bleach in the presence of different amounts of various organic load materials. The ability of this RNA to be amplified was then tested using real-time TMA. Organic load materials included Amplification, Hybridization, Enzyme and Selection Reagents from the APTIMA COMBO 2® Assay kit (Catalog No. 1032; Gen-Probe Incorporated; San Diego, Calif.), and mixtures thereof, urine transport medium (UTM; Catalog No. 1040 APTIMA COMBO 2® Assay Urine Specimen Collection Kit for Male and Female Urine Specimens; Gen-Probe Incorporated), swab transport medium (STM), KOVA-Trol™ (Hycor Biomedical Inc.; Garden Grove, Calif.), bovine serum albumin (BSA), lithium lauryl sulfate (LLS) and human plasma. Of these compounds, UTM and Enzyme Reagent were most effective at interfering with reaction of the bleach with RNA. In one experiment, 20% commercial bleach was required to overcome the effects of UTM, which is in contrast to the very rapid and complete reaction of rRNA with 0.016% bleach in the absence of organic load materials (FIGS. 10A-10F).

B. PAGE Results

PAGE was performed using a procedure similar to that disclosed in Example 1. Briefly, a known amount of a 71-mer oligonucleotide was incubated with a formulation having a known concentration of candidate reagent. A 1× volume of 2×TBE-urea loading buffer (180 mM Tris, 180 mM boric acid, 4 mM EDTA, pH 8.0) was added to the mixture solution and vortexed for 10 seconds. Ten microliters of sample was loaded in each lane of a 10% polyacrylamide TBE-Urea gel. The gel was run in 1×TBE running buffer at 180 V for 35 to 40 minutes depending on the length of oligonucleotide. The gel then was removed from the cast and stained in 1/10,000 SYBr Green I dye solution for 20 minutes. The stained gel was imaged using a ChemiImager™ 4400.

Oligonucleotides were reacted with bleach in the presence of various concentrations of organic load compounds, and reaction products were analyzed by PAGE. Serum, Amplification Reagent and the NALC in Enzyme Dilution Buffer interfered with the reaction of bleach with the oligonucleotide (FIGS. 11A-11D).

C. RP-HPLC Results

Reverse phase (RP) HPLC was utilized to characterize nucleic acids exposed to deactivation solutions using standard procedures. Specifications for the HPLC apparatus and methodology utilized were as follows. A ZORBAX® Eclipse XDB C-8 Reverse Phase Column (Agilent Technologies, Inc.; Palo Alto, Calif.) having a 4.6 mm internal diameter and a 15 cm length was utilized. Triethyl ammonium acetate (TEAA)/acetonitrile was utilized as the mobile phase, where Buffer A contained 0.1 M TEAA and Buffer B contained 100% acetonitrile. A gradient of 5%-100% Buffer B was utilized in a time interval of 15 minutes at a flow rate of 0.5 ml/min. 50 µL oligonucleotide samples having an optical density of 2.0 OD (oligonucleotide 26mer=10 µM) were injected on the column and column output was detected at a wavelength of 254 nm.

Reaction of bleach with a 26mer DNA oligomer in the presence of NALC and subsequent chromatography using RP-HPLC revealed that NALC interfered with the reaction of bleach with DNA. These results confirmed PAGE findings in Example 6.

D. Conclusions

Materials that effectively interfered with the reaction of bleach with nucleic acids were Urine Transport Medium (UTM) and the NALC in Enzyme Dilution Buffer (EDB). Materials that moderately interfered with the reaction of bleach with nucleic acids were Swab Transport Medium (STM), Hybridization Reagent, Amplification Reagent and human serum. Materials that weakly interfered with the reaction of bleach with nucleic acids (or not at all) were Selection Reagent, APTIMA COMBO 2® Assay Target Capture Reagent, lithium lauryl sulfate and KOVA-Trol™. From this analysis, it was determined that organic load material, especially materials containing primary amine and sulfhydryl groups, reacted with bleach and consumed it so that it was not all available to deactivate the nucleic acids. Loss of decontamination power of bleach at lower concentrations was not due to slow reaction rates or the need for excess hypochlorite over nucleotides, but rather consumption of bleach by other compounds.

Example 11

Further Screens of Alternative Formulations and Conditions

Alternative formulations to bleach, such as solutions containing dichloroisocyanuric acid (DCC) or hydrogen peroxide and copper ions, were characterized in Examples 3 and 4 by PAGE. These and additional alternative formulations were characterized by PAGE and other assays as described hereafter.

A. PAGE Results

A 71-mer oligonucleotide was reacted with various candidate compounds and the products were analyzed using PAGE. Solutions containing DCC or hydrogen peroxide with copper sulfate were tested, among other formulations. As shown in Example 3, DCC, which is less corrosive than bleach, was as effective as bleach for deactivating the oligonucleotide, if not more so. The effects of scavengers including Enzyme Dilution Buffer (EDB) and serum on DCC were also tested and compared with their effects on bleach. Similar effects were observed as shown in FIG. 12 (results are for EDB; serum results not shown). As shown in Examples 4, 5 and 7, a solution containing hydrogen peroxide and copper sulfate, which was odorless and non-corrosive, was reasonably effective at (1) changing oligonucleotide migration or oligonucleotide band retention, and (2) overcoming the effects of organic load.

Other candidate solutions were characterized by incubating them with oligonucleotide and analyzing the resulting reaction products by PAGE. The following reagents exhibited little or no changes to nucleic acid migration or band intensity in this assay: (1) peroxymonosulfate ($KHSO_5$) with or without copper sulfate; (2) perborate; (3) percarbonate; (4) hydrogen peroxide with KBr; and (5) NUCLEOCLEAN™ (Chemicon International, Inc.; Temecula, Calif.).

B. RP-HPLC Results

The RP-HPLC retention shift assay (described previously) was used to screen several bleach alternative candidates in the presence or absence of organic load material (NALC). Following is a summary of the efficacy of the alternative formulations tested as compared to 10% bleach, where "=" is roughly equivalent, "<" is less effective and ">" is more effective.

| Bleach Alt. Reagent | Organic Load | Effectiveness |
|---|---|---|
| a) NaBr/NaOCl | 70 mM NALC | > |
| b) KBr/peroxomonosulfate | 70 mM NALC | < |
| c) ClO2 | 70 mM NALC | < |
| d) 10% bleach/peroxide | 70 mM NALC | = |
| e) Citric Acid | None | < |
| f) citric acid/peroxide | None | < |
| g) 10% bleach/citric acid/peroxide | 70 mM NALC | = |
| h) 10% bleach/peroxide/ sodium hydroxide | 70 mM NALC | = |
| i) phosphoric acid/peroxide | None | < |
| j) peroxide/CuSO$_4$ | None | =, > |
| k) peroxide/CuSO$_4$ | 70 mM NALC | =, > |
| l) peroxide/CuSO$_4$/phosphoric acid | 70 mM NALC | < |
| m) 10% bleach/peroxide | 70 mM NALC | = |
| n) Citric Acid | None | < |

Formulations determined by the assay as more effective than 10% bleach are shown in bold text. Accordingly, formulations comprising (a) NaBr/NaOCl or (b) peroxide/CuSO$_4$ were as effective or more effective for deactivating nucleic acids as compared to bleach alone under the conditions of this experiment.

C. Capillary Electrophoresis Results

Ribosomal RNA was reacted with various candidate formulations in solution and the products were analyzed using a capillary electrophoresis assay. In the assay, 1 mM dichloroisocyanurate (DCC) and 17.5 mM peroxymonosulfate VIRKON® S; DuPont Animal Health Solutions, United Kingdom), tested separately, substantially eliminated peaks corresponding to 0.72 mM rRNA oligonucleotide. In situ-generated $Cl_2$ (10 mM peroxymonosulfate +20 mM KCl) partially eliminated 72 µM rRNA oligonucleotide. Tested separately, (a) in situ-generated $Br_2$ (10 mM peroxymonosulfate +20 mM KBr), (b) between 10 and 100 µM dichloro-hydantoin or dibromo-hydantoin, (c) between 10 and 100 µM hypobromite, and (d) 10 mM peroxymonosulfate +metal ions (1 mM $Cu^{2+}$, 1 or 10 mM $Fe^{2+}$) substantially eliminated 72 µM rRNA oligonucleotide.

D. Real-Time TMA Results

Ribosomal RNA was reacted with various compounds in solution, and the ability of the RNA to be amplified was then tested using the real-time TMA assay described in Example 8. The efficacies of certain formulations are described hereafter.

VIRKON® S (peroxymonosulfate). The nucleic acid was reacted with a 2.5% VIRKON® S solution (about 8.7 mM peroxymonosulfate), which was a substantially lower concentration than the organic load included in the reaction (Enzyme Dilution Buffer (EDB) or Urine Transport Medium (UTM) here). Thus, 2.5% VIRKON® S solution did not substantially inactivate the nucleic acid target in the presence of 5 µL EDB or UTM. DCC. An 83 mM DCC solution, which was determined as approximately equivalent to 10% bleach, inactivated target in the presence of EDB. Peroxymonosulfate/KBr. Target rRNA in the presence of UTM was inactivated with 0.25 M peroxymonosulfate/0.25 M KBr. Other ratios tested were not as effective, and an optimum ratio is determined by varying the ratio in additional runs of the assay. At 0.25 M of each component, intensive coloration and odor were observed (due to the $Br_2$), and after addition to UTM/Target mix, a residue formed. The residue dissolved upon a 50X dilution in water. The stability of this formulation may be characterized further by varying reaction conditions in additional runs of the assay. If formulations including these components are found to have limited stability, they can be provided in dry powder formulations and the solutions can be prepared shortly before use. Perborate and percarbonate. Perborate was not sufficiently soluble at concentrations useful in solution. Percarbonate was soluble to 880 mM (roughly the equivalent of 3% peroxide). When combined with copper(II), percarbonate at this concentration reacted with nucleic acid essentially with the efficacy of 3% hydrogen peroxide. Percarbonate evolved oxygen quite readily when mixed with copper(II), however, indicating the stability of the active reagents would require additional testing by the assay. Also, when percarbonate was combined with copper(II)/piperazine, a yellow residue formed. Enhanced activity was observed in solution (as with hydrogen peroxide/copper(II)/piperazine), but the solution characteristics were not ideal (lower solubility, foamy). Accordingly, while the percarbonate solutions were effective nucleic acid deactivators, the solution properties were less favorable than hydrogen peroxide formulations. Provision of the components in dry form to prepare solutions just prior to use would overcome some of these disadvantages.

From these results, the compounds that were especially effective (at appropriate concentrations) included bleach+peroxide, $KHSO_5$+KBr, DCC and peroxide+UTM. Compounds that were not as effective under the particular conditions of the experiments include 15% peroxide alone; peroxide+potassium, sodium or iron ions; 5 mM bromo- or chloro-hydantoin and $KMnO_4$. The effectiveness of peroxide+copper was not determined at the time of these studies since the corresponding control failed (i.e., the reaction mix itself inhibited TMA). It also was determined 1 mM $CuSO_4$/3% $H_2O_2$ inactivated rRNA oligonucleotide to a greater degree than 1 mM $CuBr_2$/3% $H_2O_2$, $CuCl_2$/3% $H_2O_2$, or $Cu(NO_3)_2$/3% $H_2O_2$. Additionally, 1 mM $Cu(OAc)_2$/3% $H_2O_2$ inactivated rRNA to a greater degree than 1 mM $CuSO_4$/3% $H_2O_2$.

Results from the analytical methods described herein are summarized in the following Table. In the Table, "+" indicates the compound was deactivating; "−" indicates the compound was not substantially deactivating under the conditions and by the methods used; "*"indicates equivocal results were obtained and further results can be obtained by repeating the assay at the conditions shown; no notation indicates the conditions were not examined by the indicated assay.

| Compound | Bioanalyzer | TMA | HPLC, MS | PAGE |
|---|---|---|---|---|
| HOCl | + | + | + | + |
| HOBr | + | | | |
| $Cl_2$ (from peroxymonosulfate + KCl) | − | | | |
| $Br_2$ (from peroxymonosulfate + KBr) | + | + | − | |
| $I_2$ (from peroxymonosulfate + KI) | − | | | |

-continued

| Compound | Bioanalyzer | TMA | HPLC, MS | PAGE |
|---|---|---|---|---|
| DCC (ACT 340 PLUS 2000 ® DISINFECTANT) | + |  | + | + |
| DCC |  | + |  | + |
| halo-hydantoins | + | + |  |  |
| HOCl + tertiary amines | − |  |  |  |
| NaBr + NaOCl |  |  | + |  |
| ClO$_2$ |  |  | − |  |
| H$_2$O$_2$ |  | − | − | − |
| H$_2$O$_2$ + metal ions |  |  | + | + |
| H$_2$O$_2$ + metal ions + ascorbate |  |  | + |  |
| H$_2$O$_2$ + HOCl | − |  | − |  |
| H$_2$O$_2$, acidic |  |  | − |  |
| H$_2$O$_2$, acidic + metal ions |  |  | + |  |
| H$_2$O$_2$, acidic + HOCl (two step addition) |  |  | − |  |
| H$_2$O$_2$, basic + HOCl (two step addition) |  |  | − |  |
| H$_2$O$_2$ + KBr or NaCl |  | − | − |  |
| Chloramine-T | − |  |  |  |
| peracetic acid (Peroxill 2000 ®) | − |  |  |  |
| perborate |  |  | − | − |
| percarbonate |  | * |  | − |
| VIRKON ® S solution (peroxymonosulfate) | +/− | − |  |  |
| peroxymonosulfate | + | + |  |  |
| peroxymonosulfate + Cu(II) |  |  |  | − |
| DNA AWAY ™ solution | − |  |  |  |
| DNA-OFF ™ cleansing solution | − |  |  |  |
| DNAZAP ™ decontamination solution | + |  |  |  |
| NUCLEOCLEAN ™ decontamination solution |  |  | − | − |
| Citric acid |  |  | − |  |

In this Table, DNA AWAY™ is an alkali hydroxide solution (Molecular BioProducts, Inc., San Diego, Calif.; Cat. No. 7010), DNAZAP™ is a pair of PCR DNA degradation solutions (Ambion, Inc., Austin, Tex.; Cat. No. 9890), DNA-OFF™ is a non-alkaline cleaning solution (Q-biogene, Inc., Irvine, Calif.; Cat. No. QD0500), and NUCLEOCLEAN™ is a PCR decontamination solution (Chemicon International, Temecula, Calif.; Cat. No. 3097S). These results showed bleach (at reduced levels), dichloroisocyanurate (DCC), H$_2$O$_2$/ Cu(II), peroxymonosulfate, peroxymonosulfate/KBr (generates Br$_2$) and hypobromite displayed especially potent nucleic acid deactivation activity in solution.

Example 12

Further Characterization of Nucleic Acid Deactivation Formulations and Methods in a Nucleic Acid Amplification Procedure Multiple formulations and various methods of applying them were characterized for nucleic acid deactivation efficacy in an APTIMA COMBO 2® Assay (described hereafter) and associated components. Following is a list of materials utilized for the assay and characterization process.

Amplification Reagent
Amplification Reconstitution Solution
Target Capture Reagent
Target Capture Reagent B
CT Positive Control
GC Positive Control
Oil Reagent
Wash Buffer
Urine Transport Media (UTM)
Swab Transport Media (STM)
Enzyme Reagent
Enzyme Reconstitution Solution
CT rRNA
GC rRNA
KOVA-Trol™ (Normal)
Probe Reagent
Probe recon Solution
Selection Reagent
Detection Reagent I
Detection Reagent II
Endocervical swabs
Household liquid bleach (Chlorox®)
Dichloroisocyanurate (DCC)
Household hydrogen peroxide, 3% U.S.P. (H$_2$O$_2$)
Cupric sulfate (Cu(II))
Peroxymonosulfate (KHSO$_5$)

Following is a description of several analytical processes employed for the characterization procedures.

A. Preparation of Positive and Negative Amplification Reactions

Oil reagent (200 microliters) was added to 80 reaction tubes (12×75 mm). 4.2×10$^{10}$ copies of *Chlamydia trachomatis* (CT) and *Neisseria gonorrhoeae* (GC) rRNA were spiked into 3.15 ml of reconstituted Amplification Reagent. Seventy-five microliters (1×10$^9$ copies (~2.5 ng)) of this spiked Amplification Reagent was added to 40 of the reaction tubes (positive samples). Seventy-five microliters of Amplification Reagent without target (negative samples) was added to the other 40 tubes. All 80 samples were incubated for 10 min at 62° C., then 5 min at 42° C. Twenty-five microliters of reconstituted Enzyme Reagent was added to each tube, the rack was removed from the water bath, the rack was shaken to mix tube contents, and the rack then was quickly returned to the water bath. Reaction tube contents were incubated 60 min at 42° C. (amplification), then for 10 min at 80° C. (inactivation of enzymes). Thirty-eight of the positive samples and 38 of the negative samples were pooled and oil was removed from each pool. The two remaining positive and negative samples were assayed according to the standard APTIMA COMBO 2® manual assay protocol (described above).

B. Preparation of CT+GC rRNA Samples

5×10$^8$ copies of CT and GC rRNA prepared by standard procedures were added to 100 microliters of UTM:KOVA-Trol™ in a 1:1 ratio (in some cases (indicated in the table below), samples were added to 100 microliters of STM). The desired number of replicates of this mixture can be prepared as a pool before spotting on the surface.

C. Deacontamination Assay Protocol

Surface. Decontamination assays were performed on 2×4 ft sections of ChemSurf laboratory bench ("surface"). Before, between and after the various experiments, the surface was cleaned with a 50% bleach solution (household liquid bleach (e.g., ULTRA CLOROX® BLEACH) diluted 1:1 with water) followed by a water rinse. Wiping was accomplished with paper towels or large Kimwipes.

Sample application. One-hundred microliters of each selected sample (see below) was applied to the surface in a circular spot of about 1.5 inches in diameter. Approximately eight samples were applied, evenly spaced, on the surface. Samples were allowed to dry for approximately 15-30 min.

Sample collection. A Gen-Probe Incorporated endocervical swab was placed in 3 ml of Swab Transport Medium (STM) in a transport tube labeled with the name of the sample to be collected. The swab was removed from the transport tube and, using a circular motion, each spot was swabbed where the sample was applied. Each swab was returned to its transport tube, the end of the swab was carefully snapped-off at the scoreline, and the tube was closed using its penetrable cap, and then vortexed.

Deactivation formulations tested. Among the formulations tested were:

| a) 10% bleach | one application |
|---|---|
| b) 10% bleach | two applications |
| c) 40 mM DCC | one application |
| d) 40 mM DCC | two applications |
| e) 3% $H_2O_2$, 1 mM Cu(II) | one application |
| f) 3% $H_2O_2$, 1 mM Cu(II) | two applications |
| g) 1% $H_2O_2$, 1 mM Cu(II) | one application |
| h) 1% $H_2O_2$, 1 mM Cu(II) | two applications |
| i) 200 mM $KHSO_5$ | one application |
| j) 200 mM $KHSO_5$ | two applications. |

Decontamination protocol. The decontamination protocol utilized included the following steps.

1) The surface was cleaned (see above).

2) For negative controls a sample was collected from a circular area of ~1.5 inch in diameter, selected randomly on the surface, before any positive samples were applied to the surface.

3) Approximately eight replicate CT & GC rRNA in UTM: KOVA-Trol™ (1:1) (or STM) samples (100 microliters each) were spotted and evenly spaced on the surface.

4) Spot 1 was treated with decontamination condition "a" above (10% bleach, one application) as follows: the area containing the sample (about 7×7 inch square with sample in the center) was wetted with approximately 2 ml of reagent (in some cases (indicated in table below) approximately 3 ml was used) and then immediately wiped with a paper towel or large Kimwipe until it was dry (the towel sometimes was flipped over during the process if necessary to complete the drying). The towel and the glove that was on the hand that performed the wiping were carefully discarded (the other glove was discarded if there was a possibility it became contaminated). A sample from the original spot of application was collected using an endocervical swab as described above.

5) Spot 2 was treated with condition "b" using the same general method described in "4" above, but also with a second application of the decontamination reagent.

6) The sample spots then were treated with the decontamination conditions listed above until all samples on the surface were treated.

7) The surface was cleaned as described above, and a sufficient number of sample replicates were applied to complete testing of the decontamination conditions plus one additional spot (to be used as a positive control).

8) Testing of decontamination conditions then was completed.

9) For last remaining sample spot (positive control), the spot was swabbed directly without any application of decontamination reagent.

10) Steps 1-9 were completed for the negative amplification and the positive amplification samples.

Assay protocol. Replicates (2×400 μL) of each of the samples collected in the decontamination studies described above were assayed using an APTIMA COMBO 2® Assay (Catalog No. 1032; Gen-Probe Incorporated; San Diego, Calif.), described below. The assay amplified *Chlamydia trachomatis* (referred to herein as "CT" or "Ctr") and *Neisseria gonorrhoeae* (referred to herein as "GC" or "Ngo") template rRNA prepared by standard methodology ("positive Amp") and also was run without template rRNA ("negative Amp"). The assay was performed using the following general protocol:

1. Reconstitute reagents using the docking collars. Reconstitute Amplification Reagent with Amplification Reconstitution Solution, Enzyme Reagent with Enzyme Reconstitution Solution, and Probe Reagent with Probe Reconstitution Solution.
2. Dilute Target Capture Reagent (TCR) Component B into Target Capture Reagent at a 1:100 dilution and mix well by hand.
3. Dispense 100 μL of the TCR:Component B mix into each reaction tube of a Ten-Tube Unit (TTU, Catalog No. TU002; Gen-Probe Incorporated).
4. Pierce the cap and pipette 400 μL of the controls into the appropriate tube in the following order: Tube 1 (CT Positive Control) then Tube 2 (GC Positive Control).
5. Transfer 400 μL of each sample into the appropriate tube of the TTU.
6. When all samples are loaded in an appropriate rack (Catalog No. 4579; Gen-Probe Incorporated), place a sealing card on the TTU, and mix the samples by gently shaking by hand. Do not vortex the rack.
7. Incubate at 62° C. in a water bath for 30 minutes.
8. Place the rack on the bench and incubate for 30 minutes.
9. Load a Target Capture System (TCS, Catalog No. 5210, Gen-Probe Incorporated) with Ten-Tip cassettes (Catalog No. 4578; Gen-Probe Incorporated). Ensure that the wash bottle is connected to the pump.
10. Prime the pump lines with two flushes of Wash Reagent.
11. Place the rack on the TCS magnetic base, remove sealing cards and cover with new cards (do not stick down). Incubate for 5 minutes.
12. Turn on the vacuum for the aspirator. The vacuum gauge must read between 9 and 11 in. Hg with the system correctly set up. Aspirate all liquid by lowering the aspiration manifold slowly into the bottom of the tubes. Tap the bottom of the tubes with the tips briefly. Avoid holding the tips at the bottom of the tube. Aspirate until the all foam is removed from the tube.
13. Add 1.0 ml of Wash Reagent into each tube, by pumping the wash bottle once.
14. Cover tubes with a sealing card and vortex on the multi-vortexer.
15. Place rack on the TCS magnetic base for 5 minutes.
16. Aspirate all liquid.
17. Add 75 μL of the reconstituted Amplification Reagent.
18. Add 200 μL of Oil Reagent.
19. Cover tubes with a sealing card and vortex on the multi-vortexer.
20. Incubate the rack in a 62° C. water bath for 10 minutes.
21. Transfer the rack to a circulating water bath at 42° C. and incubate for 5 minutes.
22. With the rack in the water bath, remove the sealing card, and add 25 μL of the Enzyme Reagent to all of the reactions.
23. Immediately cover with a sealing card, briefly remove from the waterbath, and mix the reactions, gently shaking by hand.
24. Incubate the rack at 42° C. for 60 minutes.
25. Remove the rack from the water bath and transfer to the HPA area. Add 100 μL of the reconstituted Probe Reagent.
26. Vortex on the multi-vortexer.
27. Incubate the rack in a circulating water bath at 62° C. for 20 minutes.

28. Remove the rack from the water bath and incubate on the bench-top, at room temperature, for 5 minutes.
29. Add 250 µL of Selection Reagent.
30. Cover tubes with a sealing card and vortex on the multi-vortexer.
31. Incubate the rack at 62° C. in a circulating water bath for 10 minutes.
32. Incubate the rack on the bench-top, at room temperature, for 15 minutes.
33. Light-off the reactions in a LEADER® HC+ Luminometer (Catalog No. 4747; Gen-Probe Incorporated) Combo software.

Before assay, Ngo/Ctr rRNA samples were prepared by spiking amplification-negative samples with 0.5 fg of CT rRNA (about $2\times10^2$ copies) and 50 fg of GC rRNA (about $2\times10^4$ copies). In addition, 5-10 negative assay controls (STM only) were performed. Acceptance criteria were as follows.

| Controls | Specifications |
| --- | --- |
| Amplification Positive Control, CT | CT Positive, GC Negative |
| Amplification Positive Control, GC | CT Negative, GC Positive |

| Samples | Specifications |
| --- | --- |
| Negative control (swipes from clean, control area) | CT Negative, GC Negative |
| Positive control (swipes from sample spot w/no cleaning) | CT Positive, GC Positive |
| rRNA and positive amplicon swipes (cleaned areas) | CT Negative, GC Negative |
| Negative amplicon (cleaned areas) | CT Positive, GC Positive |

Follow-up Testing. Any samples not meeting the above specifications were stored at room temperature and re-tested the following day. The acceptance criteria for the follow-up testing are the same as the acceptance criteria for the initial testing (see above).

D. Characterization Results of Nucleic Acid Deactivation Using Various Formulations and Application Methods The following table depicts results collected using the protocols described above. "NA Source" is the nucleic acid source, "# App" is the number of reagent applications, "kRLU" is relative light units times a factor of 1000, and "pip" is piperazine, Expected Ctr and Ngo results are negative (Neg) for Ngo/Ctr rRNA, Neg for Pos Amplification and positive (Pos) for Neg Amp. The majority of Ctr and Ngo results from the test were valid, and invalid results are not included in the Table.

| Effectiveness of Reagents Used for Surface Decontamination | | | | | |
| --- | --- | --- | --- | --- | --- |
| Reagent | NA Source | # App | kRLU | Ctr Result | Ngo Result |
| 10% Bleach | Ngo/Ctr rRNA | 1 | 10 | Neg | Neg |
| " | " | " | 6 | Neg | Neg |
| " | " | 2 | 5 | Neg | Neg |
| " | " | " | 3 | Neg | Neg |
| " | " | 1 | 3 | Neg | Neg |
| " | " | " | 3 | Neg | Neg |
| " | " | 2 | 2 | Neg | Neg |
| " | " | " | 2 | Neg | Neg |
| " | Positive Amplification (100 µL) | 1 | 3 | Neg | Neg |
| " | Positive Amplification (100 µL) | " | 3 | Neg | Neg |
| " | Positive Amplification (100 µL) | 2 | 3 | Neg | Neg |
| " | Positive Amplification (100 µL) | " | 3 | Neg | Neg |
| " | Positive Amplification (100 µL) | 1 | 2 | Neg | Neg |
| " | Positive Amplification (100 µL) | " | 2 | Neg | Neg |
| " | Positive Amplification (100 µL) | 2 | 3 | Neg | Neg |
| " | Positive Amplification (100 µL) | " | 2 | Neg | Neg |
| " | Negative Amplification (100 µL) | 1 | 828 | Pos | Pos |
| " | Negative Amplification (100 µL) | " | 859 | Pos | Pos |
| " | Negative Amplification (100 µL) | 2 | 825 | Pos | Pos |

Effectiveness of Reagents Used for Surface Decontamination

| Reagent | NA Source | # App | kRLU | Ctr Result | Ngo Result |
|---|---|---|---|---|---|
| " | Negative Amplification (100 µL) | " | 870 | Pos | Pos |
| " | Negative Amplification (100 µL) | 1 | 1004 | Pos | Pos |
| " | Negative Amplification (100 µL) | " | 1020 | Pos | Pos |
| " | Negative Amplification (100 µL) | 2 | 996 | Pos | Pos |
| " | Negative Amplification (100 µL) | " | 1008 | Pos | Pos |
| 10% Bleach, 0.1M Bicarb, 0.025% LLS | Ngo/Ctr rRNA | 1 | 9 | Neg | Neg |
| 10% Bleach, 0.1M Bicarb, 0.025% LLS | " | " | 9 | Neg | Neg |
| 10% Bleach, 0.1M Bicarb, 0.025% LLS | " | 2 | 10 | Neg | Neg |
| 10% Bleach, 0.1M Bicarb, 0.025% LLS | " | " | 10 | Neg | Neg |
| 10% Bleach, 0.1M Bicarb, 0.025% LLS | " | 1 | 10 | Neg | Neg |
| 10% Bleach, 0.1M Bicarb, 0.025% LLS | " | " | 10 | Neg | Neg |
| 10% Bleach, 0.1M Bicarb, 0.025% LLS | " | " | 12 | Neg | Neg |
| 10% Bleach, 0.1M Bicarb, 0.025% LLS | " | " | 11 | Neg | Neg |
| 10% Bleach, 0.1M Bicarb, 0.025% LLS | " | 2 | 10 | Neg | Neg |
| 10% Bleach, 0.1M Bicarb, 0.025% LLS | " | " | 11 | Neg | Neg |
| 10% Bleach, 0.1M Bicarb, 0.025% LLS | Positive Amplification (100 µL) | 1 | 10 | Neg | Neg |
| 10% Bleach, 0.1M Bicarb, 0.025% LLS | Positive Amplification (100 µL) | " | 11 | Neg | Neg |
| 10% Bleach, 0.1M Bicarb, 0.025% LLS | Positive Amplification (100 µL) | 2 | 11 | Neg | Neg |
| 10% Bleach, 0.1M Bicarb, 0.025% LLS | Positive Amplification (100 µL) | " | 11 | Neg | Neg |
| 10% Bleach, 0.1M Bicarb, 0.025% LLS | Positive Amplification (100 µL) | 1 | 8 | Neg | Neg |
| 10% Bleach, 0.1M Bicarb, 0.025% LLS | Positive Amplification (100 µL) | " | 8 | Neg | Neg |
| 10% Bleach, 0.1M Bicarb, 0.025% LLS | Positive Amplification (100 µL) | 2 | 10 | Neg | Neg |
| 10% Bleach, 0.1M Bicarb, 0.025% LLS | Positive Amplification (100 µL) | " | 12 | Neg | Neg |
| 10% Bleach, 0.1M Bicarb, 0.025% LLS | Positive Amplification (100 µL) | 1 | 9 | Neg | Neg |
| 10% Bleach, 0.1M Bicarb, 0.025% LLS | Positive Amplification (100 µL) | " | 7 | Neg | Neg |
| 10% Bleach, 0.1M Bicarb, 0.025% LLS | Positive Amplification (100 µL) | 2 | 11 | Neg | Neg |
| 10% Bleach, 0.1M Bicarb, 0.025% LLS | Positive Amplification (100 µL) | " | 11 | Neg | Neg |

-continued

Effectiveness of Reagents Used for Surface Decontamination

| Reagent | NA Source | # App | kRLU | Ctr Result | Ngo Result |
|---|---|---|---|---|---|
| 10% Bleach, 0.1M Bicarb, 0.025% LLS | Negative Amplification (100 μL) | 1 | 2243 | Pos | Pos |
| 10% Bleach, 0.1M Bicarb, 0.025% LLS | Negative Amplification (100 μL) | " | 2269 | Pos | Pos |
| 10% Bleach, 0.1M Bicarb, 0.025% LLS | Negative Amplification (100 μL) | 2 | 2240 | Pos | Pos |
| 10% Bleach, 0.1M Bicarb, 0.025% LLS | Negative Amplification (100 μL) | " | 2259 | Pos | Pos |
| 10% Bleach, 0.1M Bicarb, 0.025% LLS | Negative Amplification (100 μL) | 1 | 2213 | Pos | Pos |
| 10% Bleach, 0.1M Bicarb, 0.025% LLS | Negative Amplification (100 μL) | " | 2348 | Pos | Pos |
| 10% Bleach, 0.1M Bicarb, 0.025% LLS | Negative Amplification (100 μL) | 2 | 2353 | Pos | Pos |
| 10% Bleach, 0.1M Bicarb, 0.025% LLS | Negative Amplification (100 μL) | " | 2277 | Pos | Pos |
| 10% Bleach, 0.1M PB, 0.05% SDS | Ngo/Ctr rRNA | 1 | 10 | Neg | Neg |
| 10% Bleach, 0.1M PB, 0.05% SDS | " | " | 11 | Neg | Neg |
| 10% Bleach, 0.1M PB, 0.05% SDS | " | 2 | 10 | Neg | Neg |
| 10% Bleach, 0.1M PB, 0.05% SDS | " | " | 11 | Neg | Neg |
| 10% Bleach, 0.1M PB, 0.05% SDS | " | 1 | 8 | Neg | Neg |
| 10% Bleach, 0.1M PB, 0.05% SDS | " | " | 8 | Neg | Neg |
| 10% Bleach, 0.1M PB, 0.05% SDS | " | " | 11 | Neg | Neg |
| 10% Bleach, 0.1M PB, 0.05% SDS | " | " | 10 | Neg | Neg |
| 10% Bleach, 0.1M PB, 0.05% SDS | " | 2 | 9 | Neg | Neg |
| 10% Bleach, 0.1M PB, 0.05% SDS | " | " | 8 | Neg | Neg |
| 10% Bleach, 0.1M PB, 0.05% SDS | Positive Amplification (100 μL) | 1 | 11 | Neg | Neg |
| 10% Bleach, 0.1M PB, 0.05% SDS | Positive Amplification (100 μL) | " | 13 | Neg | Neg |
| 10% Bleach, 0.1M PB, 0.05% SDS | Positive Amplification (100 μL) | 2 | 7 | Neg | Neg |
| 10% Bleach, 0.1M PB, 0.05% SDS | Positive Amplification (100 μL) | " | 8 | Neg | Neg |
| 10% Bleach, 0.1M PB, 0.05% SDS | Positive Amplification (100 μL) | 1 | 12 | Neg | Neg |
| 10% Bleach, 0.1M PB, 0.05% SDS | Positive Amplification (100 μL) | " | 11 | Neg | Neg |
| 10% Bleach, 0.1M PB, 0.05% SDS | Positive Amplification (100 μL) | 1 | 11 | Neg | Neg |
| 10% Bleach, 0.1M PB, 0.05% SDS | Positive Amplification (100 μL) | " | 11 | Neg | Neg |
| 10% Bleach, 0.1M PB, 0.05% SDS | Negative Amplification (100 μL) | 1 | 2192 | Pos | Pos |
| 10% Bleach, 0.1M PB, 0.05% SDS | Negative Amplification (100 μL) | " | 2285 | Pos | Pos |

-continued

Effectiveness of Reagents Used for Surface Decontamination

| Reagent | NA Source | # App | kRLU | Ctr Result | Ngo Result |
|---|---|---|---|---|---|
| 10% Bleach, 0.1M PB, 0.05% SDS | Negative Amplification (100 μL) | 2 | 2240 | Pos | Pos |
| 10% Bleach, 0.1M PB, 0.05% SDS | Negative Amplification (100 μL) | " | 2212 | Pos | Pos |
| 10% Bleach, 0.1M PB, 0.05% SDS | Negative Amplification (100 μL) | 1 | 806 | Neg | Pos |
| 10% Bleach, 0.1M PB, 0.05% SDS | Negative Amplification (100 μL) | " | 899 | Pos | Pos |
| 10% Bleach, 0.1M PB, 0.05% SDS | Negative Amplification (100 μL) | 2 | 2218 | Pos | Pos |
| 10% Bleach, 0.1M PB, 0.05% SDS | Negative Amplification (100 μL) | " | 2193 | Pos | Pos |
| 40 mM DCC | Ngo/Ctr rRNA | 1 | 3 | Neg | Neg |
| " | " | " | 3 | Neg | Neg |
| " | " | 2 | 3 | Neg | Neg |
| " | " | " | 3 | Neg | Neg |
| " | " | 1 | 3 | Neg | Neg |
| " | " | " | 2 | Neg | Neg |
| " | " | 2 | 3 | Neg | Neg |
| " | " | " | 3 | Neg | Neg |
| " | " | 1 | 12 | Neg | Neg |
| " | Positive Amplification (100 μL) | 1 | 3 | Neg | Neg |
| " | Positive Amplification (100 μL) | " | 3 | Neg | Neg |
| " | Positive Amplification (100 μL) | 2 | 3 | Neg | Neg |
| " | Positive Amplification (100 μL) | " | 3 | Neg | Neg |
| " | Positive Amplification (100 μL) | 1 | 15 | Neg | Neg |
| " | Positive Amplification (100 μL) | 2 | 2 | Neg | Neg |
| " | Positive Amplification (100 μL) | " | 2 | Neg | Neg |
| " | Positive Amplification (100 μL) | 1 | 7 | Neg | Neg |
| " | Positive Amplification (100 μL) | " | 8 | Neg | Neg |
| " | Negative Amplification (100 μL) | 1 | 812 | Pos | Pos |
| " | Negative Amplification (100 μL) | " | 795 | Pos | Pos |
| " | Negative Amplification (100 μL) | 2 | 726 | Pos | Pos |
| " | Negative Amplification (100 μL) | " | 668 | Pos | Pos |
| " | Negative Amplification (100 μL) | 1 | 886 | Pos | Pos |
| " | Negative Amplification (100 μL) | " | 919 | Pos | Pos |
| " | Negative Amplification (100 μL) | 2 | 937 | Pos | Pos |

Effectiveness of Reagents Used for Surface Decontamination

| Reagent | NA Source | # App | kRLU | Ctr Result | Ngo Result |
|---|---|---|---|---|---|
| " | Negative Amplification (100 μL) | " | 919 | Pos | Pos |
| 3% peroxide, 1 mM CuSO$_4$ | Ngo/Ctr rRNA | 1 | 6 | Neg | Neg |
| 3% peroxide, 1 mM CuSO$_4$ | " | " | 3 | Neg | Neg |
| 3% peroxide, 1 mM CuSO$_4$ | " | 2 | 3 | Neg | Neg |
| 3% peroxide, 1 mM CuSO$_4$ | " | " | 3 | Neg | Neg |
| 3% peroxide, 1 mM CuSO$_4$ | " | 1 | 3 | Neg | Neg |
| 3% peroxide, 1 mM CuSO$_4$ | " | " | 3 | Neg | Neg |
| 3% peroxide, 1 mM CuSO$_4$ | " | 2 | 8 | Neg | Neg |
| 3% peroxide, 1 mM CuSO$_4$ | " | " | 3 | Neg | Neg |
| 3% peroxide, 1 mM CuSO$_4$ | Positive Amplification (10 μL) | " | 11 | Neg | Neg |
| 3% peroxide, 1 mM CuSO$_4$ | Negative Amplification (100 μL) | 2 | 870 | Pos | Pos |
| 3% peroxide, 1 mM CuSO$_4$ | Negative Amplification (100 μL) | " | 865 | Pos | Pos |
| 3% peroxide, 1 mM CuSO$_4$ | Negative Amplification (100 μL) | 2 | 781 | Pos | Pos |
| 3% peroxide, 1 mM CuSO$_4$ | Negative Amplification (100 μL) | " | 784 | Pos | Pos |
| 3 ml 3% peroxide, 1 mM CuSO$_4$ | Positive Amplification (10 μL) | 2 | 7 | Neg | Neg |
| 3 ml 3% peroxide, 1 mM CuSO$_4$ | Positive Amplification (10 μL) | " | 6 | Neg | Neg |
| 3% peroxide, 1 mM CuSO$_4$, 25 mM pip | Ngo/Ctr rRNA | " | 8 | Neg | Neg |
| 3% peroxide, 1 mM CuSO$_4$, 25 mM pip | " | 1 | 21 | Neg | Neg |
| 3% peroxide, 1 mM CuSO$_4$, 25 mM pip | " | " | 8 | Neg | Neg |
| 3% peroxide, 1 mM CuSO$_4$, 25 mM pip | " | 2 | 8 | Neg | Neg |
| 3% peroxide, 1 mM CuSO$_4$, 25 mM pip | " | " | 9 | Neg | Neg |
| 3% peroxide, 1 mM CuSO$_4$, 50 mM pip | Ngo/Ctr rRNA | 2 | 8 | Neg | Neg |
| 3% peroxide, 1 mM CuSO$_4$, 50 mM pip | " | " | 22 | Neg | Neg |
| 3% peroxide, 1 mM CuSO$_4$, 50 mM pip | " | 1 | 158 | Neg | Neg |
| 3% peroxide, 1 mM CuSO$_4$, 50 mM pip | " | 2 | 10 | Neg | Neg |
| 3% peroxide, 1 mM CuSO$_4$, 50 mM pip | " | " | 12 | Neg | Neg |
| 3% peroxide, 1 mM CuSO$_4$, 50 mM pip | " | " | 10 | Neg | Neg |
| 3% peroxide, 1 mM CuSO$_4$, 50 mM pip | " | " | 3 | Neg | Neg |
| 3% peroxide, 1 mM CuSO$_4$, 50 mM pip | Ngo/Ctr rRNA in STM | 2 | 10 | Neg | Neg |
| 3% peroxide, 1 mM CuSO$_4$, 50 mM pip | Ngo/Ctr rRNA in STM | " | 11 | Neg | Neg |
| 3% peroxide, 2 mM CuSO$_4$, 50 mM HEPES | Ngo/Ctr rRNA | 2 | 7 | Neg | Neg |
| 3% peroxide, 2 mM CuSO$_4$, 50 mM HEPES | Ngo/Ctr rRNA in STM | 2 | 11 | Neg | Neg |

-continued

Effectiveness of Reagents Used for Surface Decontamination

| Reagent | NA Source | # App | kRLU | Ctr Result | Ngo Result |
|---|---|---|---|---|---|
| 3% peroxide, 2 mM CuSO$_4$, 50 mM HEPES | Ngo/Ctr rRNA in STM | " | 10 | Neg | Neg |
| 3% peroxide, 2 mM CuSO$_4$, 50 mM pip (10 day Cu/pip) | Ngo/Ctr rRNA | 1 | 9 | Neg | Neg |
| 3% peroxide, 2 mM CuSO$_4$, 50 mM pip (10 day Cu/pip) | " | 2 | 10 | Neg | Neg |
| 3% peroxide, 2 mM CuSO$_4$, 50 mM pip (10 day Cu/pip) | " | " | 9 | Neg | Neg |
| 3% peroxide, 2 mM CuSO$_4$, 50 mM pip (10 day Cu/pip) | " | 1 | 7 | Neg | Neg |
| 3% peroxide, 2 mM CuSO$_4$, 50 mM pip (10 day Cu/pip) | " | 2 | 8 | Neg | Neg |
| 3% peroxide, 2 mM CuSO$_4$, 50 mM pip (10 day Cu/pip) | " | " | 8 | Neg | Neg |
| 3% peroxide, 2 mM cupric acetate | Ngo/Ctr rRNA | 2 | 11 | Neg | Neg |
| 3% peroxide, 2 mM cupric acetate | " | " | 12 | Neg | Neg |
| 3% peroxide, 2 mM cupric acetate | " | 2 | 9 | Neg | Neg |
| 3% peroxide, 2 mM cupric acetate | " | " | 9 | Neg | Neg |
| 3% peroxide, 2 mM cupric acetate | " | " | 10 | Neg | Neg |
| 3% peroxide, 2 mM cupric acetate | " | " | 10 | Neg | Neg |
| 3% peroxide, 2 mM cupric acetate | Ngo/Ctr rRNA in STM | 2 | 11 | Neg | Neg |
| 3% peroxide, 2 mM cupric acetate | Ngo/Ctr rRNA in STM | " | 10 | Neg | Neg |
| 3% peroxide, 2 mM CuSO$_4$ | Ngo/Ctr rRNA | 2 | 9 | Neg | Neg |
| 3% peroxide, 2 mM CuSO$_4$ | " | " | 9 | Neg | Neg |
| 3% peroxide, 2 mM CuSO$_4$ | " | " | 10 | Neg | Neg |
| 3% peroxide, 2 mM CuSO$_4$ | " | " | 9 | Neg | Neg |
| 3% peroxide, 2 mM CuSO$_4$ | Ngo/Ctr rRNA in STM | 2 | 10 | Neg | Neg |
| 3% peroxide, 2 mM CuSO$_4$ | Ngo/Ctr rRNA in STM | " | 9 | Neg | Neg |
| 1% peroxide, 1 mM CuSO$_4$ | Ngo/Ctr rRNA | 1 | 3 | Neg | Neg |
| 1% peroxide, 1 mM CuSO$_4$ | " | " | 3 | Neg | Neg |
| 1% peroxide, 1 mM CuSO$_4$ | " | 2 | 3 | Neg | Neg |
| 1% peroxide, 1 mM CuSO$_4$ | " | " | 3 | Neg | Neg |
| 1% peroxide, 1 mM CuSO$_4$ | " | 2 | 3 | Neg | Neg |
| 1% peroxide, 1 mM CuSO$_4$ | " | " | 2 | Neg | Neg |
| 1% peroxide, 1 mM CuSO$_4$ | " | 1 | 7 | Neg | Neg |
| 1% peroxide, 1 mM CuSO$_4$ | Positive Amplification (100 µL) | 2 | 7 | Neg | Neg |
| 1% peroxide, 1 mM CuSO$_4$ | Positive Amplification (100 µL) | " | 7 | Neg | Neg |

-continued

Effectiveness of Reagents Used for Surface Decontamination

| Reagent | NA Source | # App | kRLU | Ctr Result | Ngo Result |
|---|---|---|---|---|---|
| 200 mM KHSO$_5$ | Ngo/Ctr rRNA | 1 | 3 | Neg | Neg |
| " | " | " | 3 | Neg | Neg |
| " | " | 2 | 3 | Neg | Neg |
| " | " | " | 3 | Neg | Neg |

The results in the table show bleach-containing reatents—including those that also contain a corrosion inhibitor and a surfactant—effectively deactivated rRNA and positive and negative TMA reactions on surfaces. The same was true for solutions containing 40 mM DCC. Solutions containing peroxide and copper effectively deactivated rRNA on surfaces, and were not as efficacious as bleach for consistently decontaminating surfaces of positive or negative TMA reactions under the conditions tested. Adding piperazine or HEPES to the peroxide/copper solutions did not significantly alter deactivation performance on surfaces under the conditions tested. Peroxymonosulfate deactivated rRNA on surfaces, but not positive and negative TMA reactions under the conditions tested.

Example 13

Characterization of Nucleic Acid Deactivation Formulations

Effects of including corrosion inhibitors, surfactants and fragrances in nucleic acid deactivation formulations were assessed. Bleach, and to a lesser but still significant extent DCC, cause corrosion of metals and other materials. Nucleic acid deactivation activity of various candidate anti-corrosion compounds, including the sodium salts of phosphate (PB), borate, bicarbonate and dodecyl sulfate (SDS), were tested in solution prior to analysis using real-time TMA and PAGE (e.g., Example 8 and Example 1). Studies were performed to test the activity of bleach and DCC when mixed together with the candidate corrosion inhibitors. Phosphate at pH 6.4 and 7.5 destabilized bleach (loss of activity increased with time) whereas phosphate at pH 9.1 or 9.5 did not. The converse was true for DCC, where the higher pH phosphate's (9.1 and 9.5) were destabilizing whereas the lower pH phosphate's (6.4 and 7.5) were not. Bleach was stable in borate at pH 7.6 or 9.1 and bicarbonate at pH 9.3. SDS did not have any apparent effect on the activity of bleach.

Anti-corrosion formulations with bleach were also tested with the surface decontamination protocol described in Example 12. All formulations tested were determined to be effective, thus demonstrating the anti-corrosion agents have no apparent negative effect on bleach activity. One application ("1 app") is one application of the reagent and two applications ("2 app") is two applications of the reagent. Results from the analysis are presented hereafter.

| Reagent | Contamination Source | Result |
|---|---|---|
| 10% bleach, 100 mM Bicarb, 0.025% LLS, 1 app | rRNA(Ctr/Ngo) | validated |
| 10% bleach, 100 mM Bicarb, 0.025% LLS, 2 app | rRNA(Ctr/Ngo) | validated |
| 10% bleach, 100 mM Bicarb, 0.025% LLS, 1 app | pos. amplicon (100 ul) | validated |
| 10% bleach, 100 mM Bicarb, 0.025% LLS, 2 app | " | validated |
| 10% bleach, 100 mM Bicarb, 0.025% LLS, 1 app | neg. amplicon (100 ul) | validated |
| 10% bleach, 100 mM Bicarb, 0.025% LLS, 2 app | " | validated |
| 10% bleach, 100 mM PB, 0.05% SDS, 1 app | rRNA(Ctr/Ngo) | validated |
| 10% bleach, 100 mM PB, 0.05% SDS, 2 app | rRNA(Ctr/Ngo) | validated |
| 10% bleach, 100 mM PB, 0.05% SDS, 1 app | pos. amplicon (100 ul) | validated |
| 10% bleach, 100 mM PB, 0.05% SDS, 2 app | " | validated |
| 10% bleach, 100 mM PB, 0.05% SDS, 1 app | neg. amplicon (100 ul) | validated |
| 10% bleach, 100 mM PB, 0.05% SDS, 2 app | " | validated |

An assay for assessing corrosion was devised. The assay comprised soaking stainless steel bolts (1" long, ⅛" diameter, standard thread, hex-head stainless steel bolts) in candidate solutions and visually scoring corrosion over time. Results from the corrosion inhibition studies are summarized hereafter.

| Agent | Corrosion Inhibition |
|---|---|
| Phosphate, pH 9.1 | High |
| Phosphate, pH 9.5 | High |
| Borate, pH 7.6 | Moderate |
| Borate, pH 8.5 | Moderate |
| Bicarbonate, pH 9.3 | High |
| SDS* | Low to moderate |
| SDS + other corrosion inhibitors | SDS enhanced activity of corrosion inhibitor |

*Other detergents/surfactants (including lithium lauryl sulfate, PHOTO-FLO ®, saponin, TRITON ® X-100 and General Use Hybridization Reagent (Gen-Probe)) were tested, with similar results as for SDS.

Detergents and surfactants also were tested for effects on the physical properties of bleach solutions on surfaces. These agents decreased surface tension and allowed for more complete wetting of the surface with the bleach solution (typically 0.6% hypochlorite). To decrease foaming of the solution when applied to the surface, detergent concentration was lowered to a level that minimized foaming but retained effective surfactant qualities. SDS and LLS levels of approximately 0.005% to 0.02% (w/v) minimized foaming in this particular application.

Effects of fragrances on activity and stability of bleach and DCC also were tested. Among the fragrances tested were 2141-BG, 2145-BG, and two other custom fragrances from International Flavors and Fragrance. The fragrances exhibited no detectable effect on activity and stability of 10% bleach and DCC according to PAGE analysis. Also, the fragrances exhibited no detectable effect on corrosion inhibition of various compounds tested (e.g., phosphate and bicarbonate).

As a culmination of results for corrosion inhibitors, detergent/surfactants and fragrances, formulations of these reagents with bleach were developed. Unexpectedly, the balance between components was critical for maintaining physical stability of the solution. There were various combinations of these components that were successful in this regard. One formulation was as follows:

corrosion inhibitor/detergent/fragrance (6.7× concentrate): 600 mM bicarbonate (pH 9.3), 0.1% SDS, 0.05% 2141-BG finished decontamination reagent: 0.6% hypochlorite, 90 mM bicarbonate (pH 9.3), 0.015% SDS, 0.0075% 2141-BG.

Solutions comprising peroxide and copper were further characterized. It was discovered that UTM stimulated inactivation of rRNA in solutions containing peroxide and Cu(II). The effects of the individual components of the UTM formulation (150 mM HEPES, pH 7.6, 300 mM LLS, 10 mM $(NH_4)_2SO_4$) were examined, and it was discovered that the HEPES was responsible for the stimulation. Effects of pH and concentration on the observed inactivation of rRNA then was examined. The activity of different chemical components of HEPES (ethanol, ethanesulfonic acid and piperazine) and PIPES, a buffer similar to HEPES, also were examined. It was discovered piperazine was essentially as active as HEPES, and piperazine at a pH of 5.5 was utilized for further characterization. It also was discovered that piperazine stabilized Cu(II) in solution in a chemical configuration that maintains activity with peroxide for inactivating nucleic acids.

Example 14

Stability of Nucleic Acid Deactivation Formulations

Selected reagents were stored under a variety of conditions. At selected time points, the formulations were assayed for the ability to deactivate target nucleic acid using a solution assay, in which rRNA was incubated with reagents in solution, diluted, and an aliquot was assayed using real-time TMA (Example 8). Incubation conditions were at room temperature with no protection from light. Results are provided hereafter.

I. 40 mM $CuSO_4$/1 M Piperazine (Acetate), pH 5.5

| Incubation time (days) | Solution characteristics | Stability (% day 0) |
|---|---|---|
| 0 | Clear, royal blue | 100 |
| 1 | " | 100 |
| 7 | " | 100 |
| 13 | " | 100 |
| 41 | " | 100 |
| 63 | " | 96 |
| 70 | " | 94 |
| 139 | " | 94 |
| 185 | Getting lighter | 85 |

II. 80 mM $CuSO_4$/1 M Piperazine (Acetate), pH 5.5

| Incubation time (days) | Solution characteristics | Stability (% day 0) |
|---|---|---|
| 0 | Clear, royal blue | 100 |
| 83 | " | 100 |
| 129 | " | 100 |

III. 200 mM $CuSO_4$ (In Water)
A. Stored at Room Temperature, No Protection From Light

| Incubation time (days) | Solution characteristics | Stability (% day 0) |
|---|---|---|
| 0 | Clear, pale blue | 100 |
| 4 | " | 97 |
| 50 | " | 50 |

IV. 10% bleach/Sodium Bicarbonate/SDS/IFF
A. 10% Bleach/0.2 M Sodium Bicarbonate (pH 9.3)/0.05% SDS

| Incubation time (days) | Solution characteristics | Stability (% day 0) |
|---|---|---|
| 0 | Clear | 100 |
| 1 | " | 100 |
| 4 | " | 100 |
| 34 | " | 100 |
| 57 | " | 100 |
| 72 | " | 100 |

B. 10% Bleach/0.8 M Sodium Bicarbonate (pH 9.3)/0.020% SDS/0.025% 2141-BG

| Incubation time (days) | Solution characteristics | Stability (% day 0) |
|---|---|---|
| 0 | Clear, pale yellow. | 100 |
| 15 | " | 100 |
| 20 | " | 100 |
| 26 | " | 100 |

C. 10% Bleach/0.09 M Sodium Bicarbonate (pH 9.3)/0.015% SDS/0.0075% 2141-BG

| Incubation time (days) | Solution characteristics | Stability (% day 0) |
|---|---|---|
| 0 | Clear | 100 |
| 7 | " | 100 |
| 28 | " | 100 |
| 58 | " | 96 |
| 103 | " | 100 |
| 148 | " | 100 |
| 214 | " | 40 |
| 242 | " | 35 |

V. Sodium Bicarbonate/SDS/2141-BG (Then Added to "Fresh" Bleach)

A. 600 mM Sodium Bicarbonate (pH 9.3)/0.1% SDS/0.05% 2141-BG (6.7× Solution)

| Incubation time (days) | Solution characteristics | Stability (% day 0) |
|---|---|---|
| 0 | Clear, pale yellow; fine white particulate on bottom of tube | 100 |
| 2 | Clear, pale yellow; fine white particulate on bottom of tube | 100 |
| 31 | Increased particulates | 100 |
| 58 | Same as day 31 | 100 |
| 103 | " | 100 |
| 148 | " | 100 |
| 214 | " | 100 |
| 242 | " | 100 |
| 276 | " | 100 |
| 330 | " | 100 |

B. 600 mM Sodium Bicarbonate (pH 9.3)/0.1% SDS/0.05% 2145-BG (6.7× Solution)

| Incubation time (days) | Solution characteristics | Stability (% day 0) |
|---|---|---|
| 0 | Clear | 100 |
| 24 | " | 100 |
| 69 | " | 100 |
| 126 | " | 100 |
| 154 | " | 100 |
| 188 | " | 100 |
| 242 | " | 100 |

Example 15

Deactivation of Nucleic Acid on Laboratory Equipment

Formulations and procedures for deactivating nucleic acid on several pieces of laboratory equipment, including a vacuum trap system, an aspiration manifold, a rack and a deck, were assessed for efficacy.

A. Vacuum Trap System

A vacuum system comprising an aspiration manifold, two traps, an inline filter, and a vacuum pump connected in series by tubing was utilized for conducting an amplification assay after multiple target capture runs (both Ctr and Ngo rRNA). Contamination was assessed without adding bleach to the first trap. After the runs, swab samples were taken from various locations in the vacuum system and assayed for presence of Ctr and Ngo rRNA using the real-time TMA assay presented in Example 8. No detectable contamination with Ngo rRNA was identified outside of the first trap. Contamination with Ctr rRNA was identified in the tubing between the first and second traps, in the second trap and in the tubing between the second trap and the inline filter, and no contamination was detected after the inline filter. These results demonstrated that no detectable Ngo or Ctr rRNA escaped into the environment, and it is therefore feasible to not to include bleach in the first trap during usage.

B. Aspiration Manifold

One protocol for decontaminating a target capture aspiration manifold utilized for a TMA assay (APTIMA COMBO 2® Assay, Catalog No. 1032, Gen-Probe Incorporated, San Diego, Calif.) included the step of soaking the manifold in 50% bleach for 10 minutes followed by thorough rinsing with water. This procedure resulted in corrosion of the manifold and the relatively frequent need to replace it.

To test other decontamination protocols and agents, the manifold was intentionally contaminated, decontamination was attempted, then contamination levels measured. Each of target negative samples (10 replicates) remained negative using the contaminated manifold, demonstrating that the target capture system prevented contamination from entering new samples. In one decontamination protocol, it was discovered that leaving the manifold attached to the system and aspirating nucleic acid deactivation formulations through it successfully decontaminated the manifold. In such a procedure, it was determined 0.6% hypochlorite (10% bleach) or 40 mM DCC (followed by a water rinse) successfully decontaminated the manifold. A hydrogen peroxide/copper solution also successfully decontaminated the manifold, but this reagent was not as suitable for routine use as it could vigorously evolve oxygen when under reduced pressure in the vacuum system. It was determined that aspirating approximately 50 ml (about 5 ml per nozzle) of a 0.6% hypochlorite solution (with corrosion inhibitor, detergent and fragrance) followed by approximately 50 ml (about 5 ml per nozzle) of water, and then leaving the vacuum pump on for at least 1 minute sufficiently decontaminated the aspiration manifold.

C. Tecan Deck Decontamination

Leading bleach alternative candidates were tested for decontamination of the deck of the DTS® TECAN GENESIS System (Catalog No. 5216 or 5203; Gen-Probe Incorporated; San Diego, Calif.). The following results were observed.

| Reagent | Degree of Effectiveness |
|---|---|
| 10% bleach | 100% |
| 40 mM DCC | 100% |
| 3% peroxide, 1 mM Cupric Sulfate | 100% |

Thus, multiple formulations and procedures effectively deactivated nucleic acids that contaminated various laboratory equipment.

Example 16

Efficacy of Nucleic Acid Deactivation Formulation and Methods at Two Laboratory Sites Efficacy of two decontamination reagents and methods in a clinical laboratory setting were characterized at two sites. Reagent 1 (3% $H_2O_2$, 2 mM cupric sulfate) and Reagent 2 (0.6% hypochlorite, 90 mM bicarbonate, 0.015% SDS, 0.0075% 2141-BG), used according to the prescribed protocol provided to each site (see below), were equivalent to the protocol using 50% bleach described in the package insert for the APTIMA COMBO 2® Assay kit (Gen-Probe Incorporated Catalog No. 1032) and at http address www.gen-probe.com/pdfs/pi/IN0037-04RevA.pdf, and yielded effective nucleic acid deactivation and decontamination control for nucleic acid assay procedures in a clinical laboratory setting.

A. Materials

Following is a list of materials utilized at each site.
Reagent 1A (3% $H_2O_2$ USP grade)
Reagent 1B (copper sulfate, dry powder)
Reagent 2A (600 mM sodium bicarbonate, 0.1% wt/vol sodium dodecylsulfate, 0.05% 2415-BG fragrance)
Household bleach (~6% hypochlorite)

De-ionized (or higher quality) water
Milli-Q (or equivalent quality) water
APTIMA COMBO 2® Test Kit
Dual Positive Control (CT and GC rRNA)
Negative Control
Squirt bottle with a vented top (for Reagent 1)

B. Procedures

The following procedures were utilized at each site. For each rack of samples (up to 10 Ten-Tube Units (TTUs; Catalog No. TU0022; Gen-Probe Incorporated) run in the APTIMA COMBO 2® Assay, included were the usual two-run controls (Positive Control, CT and Positive Control, GC), two Dual Positive Controls (see Materials), 16 Negative Controls (see Materials) and up to 80 patient specimens. The assay was performed according to the standard protocol (package insert).

If the two-run controls met run control criteria, the run was valid (PASS). If one or both of the run controls did not meet run control criteria, the run was invalid (FAIL) and all results in the same run were invalid and were not reported. The run was then repeated. Also, as usual for patient samples, initial equivocal or invalid results were repeated.

Described below are the three phases of the research study. Each stage was run between 2 and 4 weeks as less than 2 weeks might not allow adequate evaluation of the decontamination protocol. Three weeks was determined as being ideal, and the maximum duration was four weeks. The entire study was expected to be completed in 9 weeks, with a maximum duration of 12 weeks. For each phase of the study, 15 racks of samples were assayed, with all containing the appropriate controls as described above.

Phase 1: The standard APTIMA COMBO 2® protocol utilizing 50% bleach was used for decontamination as described in the package insert (http address www.gen-probe.com/pdfs/pi/IN0037-04RevA.pdf). This approach was utilized to establish a baseline of results for comparison with results obtained when the test decontamination protocol was used.

Phase 2: The test decontamination protocol was utilized (see below).

Phase 3: The test decontamination protocol (see below) was utilized, except Reagent 2 was used when the protocol called for use of Reagent 1. Reagent 2 still was utilized when the protocol called for use of Reagent 2.

1. Rack Set-up

Each laboratory was instructed to utilize the following procedure for setting-up racks of samples.

1) Begin rack set-up in the standard fashion as described in the package insert.
2) Add 400 µL of the Positive Control, CT, to reaction tube 1.
3) Add 400 µL of the Positive Control, GC, to reaction tube 2.
4) Add 400 µL of the Dual Positive Control to reaction tubes 3-4.
5) Add 400 µL of the Negative Control to reaction tubes 5-20.
6) Add 400 µL of patient specimens into reaction tubes 21 up to 100.

2. General Decontamination Protocol

Each laboratory was instructed to apply good physical containment techniques in order to guard against spread of contamination in the lab while decontaminating each workspace. Each laboratory was cautioned that the glove on the hand used for cleaning would become contaminated and that touching clean objects with this hand should be avoided. It was recommended that one hand should be reserved for cleaning only and the other hand (clean) for application of reagent only. It also was recommended that used towels and gloves should be discarded in a receptacle in which they would be well-contained, making sure that no dripping occurred between the area undergoing decontamination and the receptacle.

3. Reagent Preparation

Each laboratory was instructed to prepare the following reagents using the procedures outlined below.

a) Prepare Reagent 1B (every 2 weeks)
   i) Add 30 ml of Milli-Q (or equivalent quality) water to 1 vial of Reagent 1B (dry reagent).
   ii) Tightly cap and invert 30 times. Let stand for 1 minute. Invert 30 more times. Make sure all of the dry reagent is dissolved.
   iii) Between uses (see section 2b below), store Reagent 1B (liquid) at 2-8° C. in the dark (the dry reagent can be stored at room temperature).
   iv) After 2 weeks of storage, discard Reagent 1B (liquid) and prepare a fresh solution.

b) Prepare Reagent 1 (daily)
   i) Add 150 ml of Reagent 1A to a squirt bottle with a vented top (provided).
   ii) Add 1.5 ml of Reagent 1B to the squirt bottle.
   iii) Replace top and thoroughly mix by swirling contents for 10-15 seconds
   iv) Use contents as described below. If there is any escape of Reagent 1 from the squirt bottle between uses, loosen the top and then retighten immediately before resuming use.
   v) After the last use of the day or 12 hours, whichever comes first, dispose of any remaining Reagent 1 in the squirt bottle. Prepare fresh reagent as described above when needed.

c) Prepare Reagent 2 (every 2 weeks)

The recipe provided below is for the preparation of 1 liter of Reagent 2. The actual amount made is to be determined based on the anticipated reagent usage in a given laboratory. The preparation of Reagent 2 to be used for cleaning racks and other equipment and may be performed in the vessel used for soaking.

i) Add 750 ml of de-ionized (or higher quality) water to an appropriate vessel. Add 150 ml of Reagent 2A to the vessel, followed by 100 ml of household bleach (this step can be performed in a fume hood if so desired to avoid contact with bleach fumes).
   ii) Close container and thoroughly mix by swirling contents for 15-20 seconds.
   iii) Use contents as needed.
   iv) At the end of 2 weeks, discard any unused Reagent 2 and prepare a fresh solution as described above.

4. Pre-Assay Procedures

Each laboratory was instructed to perform the following pre-assay procedures.

a) Turn on the water baths in the pre-amp area, but not the post-amp area (if the water baths are routinely left on 24 hours a day, this practice can be continued; however, the person running the APTIMA COMBO 2® Assay in a given day should not enter the post-amp area until the assay is ready to proceed in that area (see below)).

b) Clean all surfaces in the pre-amp area as follows (in the order listed):

Tecan. Using a squirt bottle, wet a paper towel with Reagent 1 until the towel is saturated but not dripping. Thoroughly wet and clean the Tecan deck with the wet towel (do not include a 1 minute incubation time as in the current standard protocol) and continue wiping until all the surfaces are dry. This may require additional wetted towels as well as dry towels. Once the surface has been cleaned and dried, repeat this procedure with a second application of Reagent 1. Do not rinse with water.

TCS Unit. Using a squirt bottle, wet a paper towel with Reagent 1 until the towel is saturated but not dripping. Thoroughly wet and clean surfaces of the TCS (Catalog No. 5202; Gen-Probe Incorporated; San Diego, Calif.) with the wet towel (do not include a 1 minute incubation time as in the current standard protocol) and continue wiping until all the surfaces are dry. This may require additional wetted towels as well as dry towels. Once the surface has been cleaned and dried, repeat this procedure with a second application of Reagent 1. Do not rinse with water.

Bench surfaces. Liberally apply Reagent 1 to the bench surface using a squirt bottle. Immediately clean the surface using a paper towel, making certain that the entire surface has been thoroughly wetted with the decontamination reagent yet taking care to not splash the reagent onto the floor, into surrounding areas, etc. Do not include a 1 minute incubation time as in the current standard protocol. Continue wiping until the entire surface is dry. This may require more than one paper towel. Repeat this procedure with a second application of Reagent 1. Do not rinse with water.

Pipettors. Using a squirt bottle, wet a paper towel with Reagent 1 until the towel is saturated but not dripping. Thoroughly clean the surfaces of the pipet with the wet towel (do not include a 1 minute incubation time as in the current standard protocol) and continue wiping until the pipet is dry. Repeat this procedure with a second application of Reagent 1. Do not rinse with water.

c) When finished cleaning the pre-amp area, carefully discard both gloves. Change gloves sooner if there is any suspicion of possible cross contamination.

5. Post-specimen Preparation Procedures

Each laboratory was instructed to perform the following post-specimen preparation procedures.

a) Carefully discard gloves used during specimen preparation and replace with clean gloves.
b) Clean the Tecan, items to be soaked (see below), bench surfaces used in specimen processing area and any pipettors used as follows:
  i) Tecan. Clean with Reagent 1 as described above and carefully discard both gloves.
  ii) Items to be soaked. After use, completely submerge racks, reagent reservoirs, deck plates, disposable tip racks and waste chute (and any other items that you currently soak) in Reagent 2 and allow to soak for 30-60 minutes. Rinse thoroughly with running water (do not soak in a bath of rinse water) and then dry completely with paper towels (air drying is acceptable). Carefully discard both gloves.
  iii) Bench surfaces. Clean with Reagent 1 as described above. Carefully discard both gloves
  iv) Pipettors. Clean with Reagent 1 as described above. Carefully discard both gloves 6. Post-target Capture Procedures Each laboratory was instructed to employ the following post-target capture procedures.

a) Aspiration manifold. Place a new Ten-Tip Cassette (TTC; Catalog No. 4578; Gen-Probe Incorporated) into the TCS. Turn on the vacuum pump. Carefully attach the manifold to the tips in the TTC. Carefully aspirate all Wash Solution remaining from the APTIMA COMBO 2® Assay run from the priming trough of the Wash Solution dispense station (the Wash Solution dispense manifold will have to first be moved out of the way). Add 100 ml of Reagent 2 to the trough, then carefully aspirate it through the aspiration manifold. Add 100 ml of deionized water to the trough, then carefully aspirate it through the aspiration manifold. Eject the tips into their original TTC. Leave the vacuum pump on for at least 1 minute after the last aspiration.
b) TCS, bench surfaces and pipettors. Clean with Reagent 1 as described above. Carefully discard both gloves
c) Vacuum trap waste liquid. When required (see below), decontaminate the liquid in the Waste Bottle. Attach the Waste Bottle to the TCS unit empty (i.e., do not add bleach). Use the Waste Bottle until it is 25% full (i.e., available capacity not to exceed 25%) or for 1 week (whichever is first). Remove the Waste Bottle from the system and carefully add 400 ml of undiluted bleach (if desired, this procedure can be performed in a fume hood in order to avoid release of fumes into the laboratory). Cap the Waste Bottle and gently swirl the contents until fully mixed. Incubate 5 minutes, then pour the waste into a sink. Reconnect the empty Waste Bottle to the TCS unit. Use universal precautions when handling and disposing of liquid and solid waste. Dispose of liquid and solid waste according to local, state, and federal regulations. The contents of the Waste Bottle should be treated as a potential source of assay contamination. Take precautions to avoid contaminating the work surfaces. Carefully discard both gloves.

7. Amplification Reaction b Procedures

Each laboratory was instructed to perform the following procedures after each amplfication reaction was started, which is the last step performed in the pre-amp area. After starting the reaction, each laboratory was instructed to clean the bench tops surrounding the water baths, the handles to the lids of the water baths and the pipettors using Reagent 1 according to the procedures described above. Each laboratory was instructed to carefully discard both gloves after performing these procedures.

8. Post-Amp Area Procedures

Each laboratory was provided with the following instructions concerning post-amplification each procedures. After the last cleaning in the pre-amp area was completed and new gloves were adorned, each laboratory was instructed to immediately turn on the 62° C. water bath after entering the pre-amp area. Instructions also were to pre-clean all surfaces in the post-amp area (lab benches, pipettors, handles, and others) using Reagent 2 according to the specific procedures described above, and then to carefully discard both gloves.

9. Post Amplification Procedures

Each laboratory was provided with the following instructions concerning post-amplification procedures. After adorning a clean set of gloves, instructions were provided to carefully remove the rack(s) from the 42° C. water bath, and to avoid contaminating the lid of the water bath.

10. Post Detection Procedures

Each laboratory was provided with the following instructions concerning post-detection procedures. Instructions were to (a) remove TTU's from the luminometer and deactivate reactions using the current procedure in the product insert; (b) clean all surfaces (bench surfaces, pipettors, handle on water bath lid, exterior of the LEADER® HC+Luminometer, and others) using Reagent 2 according to the specific procedures described above, (c) every two weeks, or as needed, clean the interior of the HC+with DI water as currently described in the operator's manual and soak the HC+cassettes in Reagent 2 for 30-60 minutes, and (d) carefully discard both gloves.

11. Acceptance Criteria

Each laboratory was instructed to use the following acceptance criteria.

| Controls | Specifications |
|---|---|
| Amplification Positive Control, CT | CT Positive, GC Negative |
| Amplification Positive Control, GC | CT Negative, GC Positive |
| Negative Controls | CT Negative, GC Negative |
| Dual Positive Controls | CT Positive, GC Positive |

C. Results

Reagents 1 and 2 used according to the prescribed protocol were equivalent to the protocol using 50% bleach provided with the APTIMA COMBO 2® Assay kit, and yielded effective decontamination control for the APTIMA COMBO 2® Assay in a clinical setting.

Analysis of Negative and Positive Control Data

| Laboratory | Sample | Result | Phase I | Phase II | Phase III | Total | Fisher's Exact P value |
|---|---|---|---|---|---|---|---|
| Laboratory I | Negative Control | Equivocal | 1 | 0 | 2 | 3 | 0.625 |
| | | Low Positive | 1 | 0 | 2 | 3 | |
| | | Negative | 238 | 240 | 252 | 730 | |
| | | Total | 240 | 240 | 256 | 736 | |
| | Positive Control | High Positive | 30 | 30 | 32 | 92 | |
| | | Negative | 0 | 0 | 0 | 0 | |
| | | Total | 30 | 30 | 32 | 92 | |
| Laboratory II | Negative Control | Equivocal | 1 | 0 | 0 | 1 | 0.110 |
| | | High Positive | 1 | 0 | 0 | 1 | |
| | | Low Positive | 1 | 0 | 0 | 1 | |
| | | Negative | 237 | 240 | 240 | 717 | |
| | | Total | 240 | 240 | 240 | 720 | |
| | Positive Control | High Positive | 30 | 30 | 30 | 90 | |
| | | Negative | 0 | 0 | 0 | 0 | |
| | | Total | 30 | 30 | 30 | 90 | |

When the new decontamination reagents and protocol were used, 540 of 540 (100%) control samples for Phase II and 554 of 558 (99.3%) control samples for Phase III yielded the expected results. When 50% bleach with the standard protocol was used (Phase I), 535 of 540 (99.1%) control samples yielded the expected results. A Fisher's exact test (a statistical hypothesis test method to demonstrate statistical differences between multiple groups with qualitative outcomes; Categorical Data Analysis by Alan Agresti (1990), pages 59-67, 68, 70, 78, 488, John Wiley & Sons, New York, N.Y.) was performed on the data using SAS Version 8.2 software. It is widely accepted that $P<0.05$ suggests a significant difference between groups while $P>0.05$ is indicative of no statistical difference. The Fisher's exact test yielded a p value of 0.625 for assays run at Laboratory I and 0.110 for assays run at Laboratory II. These results indicate statistical equivalence between the conditions of all three phases.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A homogenous solution for use in preventing nucleic acids from acting as templates in an amplification reaction when the solution is combined with a nucleic acid deactivating agent, the solution consisting essentially of a corrosion-inhibiting agent, a wetting agent, and a solubilizing agent, each of the agents remaining substantially in solution at 22° C.,
   wherein the wetting agent and the solubilizing agent are each needed to maintain the other agent substantially in solution in the presence of the corrosion-inhibiting agent,
   wherein the amount of each agent is such that, when combined with a nucleic acid deactivating agent in an amount sufficient for the solution to substantially deactivate nucleic acids, the corrosion-inhibiting agent reduces the corrosive properties of the deactivating agent, the wetting agent improves the dispersion properties of the deactivating agent on a solid surface and/or increases the solubility of the deactivating agent and/or other material that may be present on a solid surface or in a solution, and the solubilizing agent increases the solubility of at least one of the deactivating agent, the corrosion-inhibiting agent and the wetting agent, and
   wherein the solution does not include a nucleic acid deactivating agent;
   wherein the corrosion-inhibiting agent comprises sodium bicarbonate; the wetting agent comprises a detergent; and the solubilizing agent comprises an emulsifying agent.

* * * * *